(12) United States Patent
Gaitas

(10) Patent No.: US 9,593,808 B1
(45) Date of Patent: Mar. 14, 2017

(54) POLYMERIC MICRO-ARM APPARATUS AND METHOD TO USE THE SAME

(71) Applicant: Angelo Gaitas, Ann Arbor, MI (US)

(72) Inventor: Angelo Gaitas, Ann Arbor, MI (US)

(\*) Notice: Subject to any disclaimer, the term of this patent is extended or adjusted under 35 U.S.C. 154(b) by 1048 days.

(21) Appl. No.: 13/706,450

(22) Filed: Dec. 6, 2012

Related U.S. Application Data

(63) Continuation-in-part of application No. 13/099,351, filed on May 2, 2011, now Pat. No. 8,394,625.

(51) Int. Cl.
*G01N 33/551* (2006.01)
*F17D 3/00* (2006.01)
*G01N 33/543* (2006.01)

(52) U.S. Cl.
CPC ......... *F17D 3/00* (2013.01); *G01N 33/54366* (2013.01)

(58) Field of Classification Search
None
See application file for complete search history.

(56) References Cited

U.S. PATENT DOCUMENTS

| | | | | |
|---|---|---|---|---|
| 5,354,985 A * | 10/1994 | Quate | ............. | B82Y 20/00 250/234 |
| 5,441,343 A * | 8/1995 | Pylkki | ............. | B82Y 35/00 356/614 |
| 6,237,399 B1 * | 5/2001 | Shivaram | ........... | B82Y 35/00 73/105 |
| 6,891,151 B2 * | 5/2005 | Shimada | ............ | B82Y 20/00 250/216 |
| 6,982,419 B2 * | 1/2006 | Shimada | ............ | B82Y 20/00 369/112.29 |
| 7,323,699 B2 * | 1/2008 | Hopkins | .......... | H01L 21/30608 250/306 |
| 7,387,889 B2 * | 6/2008 | Manalis | .......... | G01N 33/54366 422/51 |
| 7,495,240 B2 * | 2/2009 | Hopkins | .......... | H01L 21/30608 250/306 |
| 7,635,392 B2 * | 12/2009 | Bloess | ............ | B82Y 15/00 250/306 |
| 7,870,616 B2 * | 1/2011 | Meister | ............ | B82Y 35/00 73/105 |
| 8,156,568 B2 * | 4/2012 | Gaitas | ............ | B82Y 35/00 250/307 |
| 8,161,568 B2 * | 4/2012 | Iyoki | ............ | B82Y 35/00 73/105 |
| 8,394,625 B2 * | 3/2013 | Gaitas | ............ | B01L 3/0217 422/501 |

(Continued)

FOREIGN PATENT DOCUMENTS

WO WO 2005114673 A1 * 12/2005 ............... B82B 3/00

*Primary Examiner* — Chris L Chin
(74) *Attorney, Agent, or Firm* — James M. Smedley LLC; James Michael Smedley, Esq.

(57) ABSTRACT

A polymeric micro-arm apparatus and method to use the same. The apparatus comprises of an elongated hollow polymeric structure with a distal end and a proximal end, an opening near the distal end, a main body attached to the polymeric structure means to move the polymeric structure, means to generate fluid flow through the opening, means to measure a flowrate of the fluid flow through the opening; and an element embedded in the polymeric structure, wherein the element is configured to detect when the polymeric structure contacts an object and measures the force that the object exerts upon the polymeric structure.

8 Claims, 25 Drawing Sheets

(56) References Cited

U.S. PATENT DOCUMENTS

| | | | | |
|---|---|---|---|---|
| 2003/0089182 A1* | 5/2003 | Thaysen | ............... | B81B 3/0021 |
| | | | | 73/862.621 |
| 2004/0208788 A1* | 10/2004 | Colton | ................... | G01Q 70/18 |
| | | | | 422/68.1 |
| 2005/0236566 A1* | 10/2005 | Liu | ........................... | B82B 3/00 |
| | | | | 250/306 |
| 2007/0237676 A1* | 10/2007 | Colton | ................... | B82Y 35/00 |
| | | | | 422/68.1 |
| 2009/0114850 A1* | 5/2009 | Hopkins | ........... | H01L 21/30608 |
| | | | | 250/492.2 |

* cited by examiner

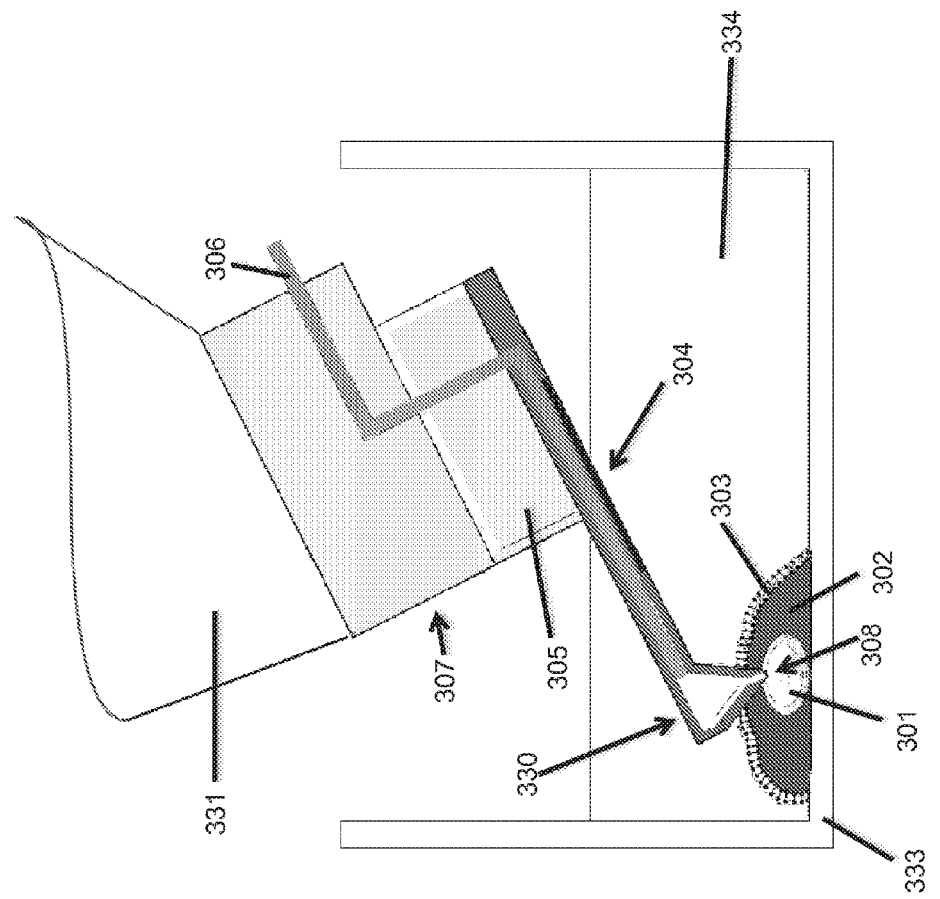

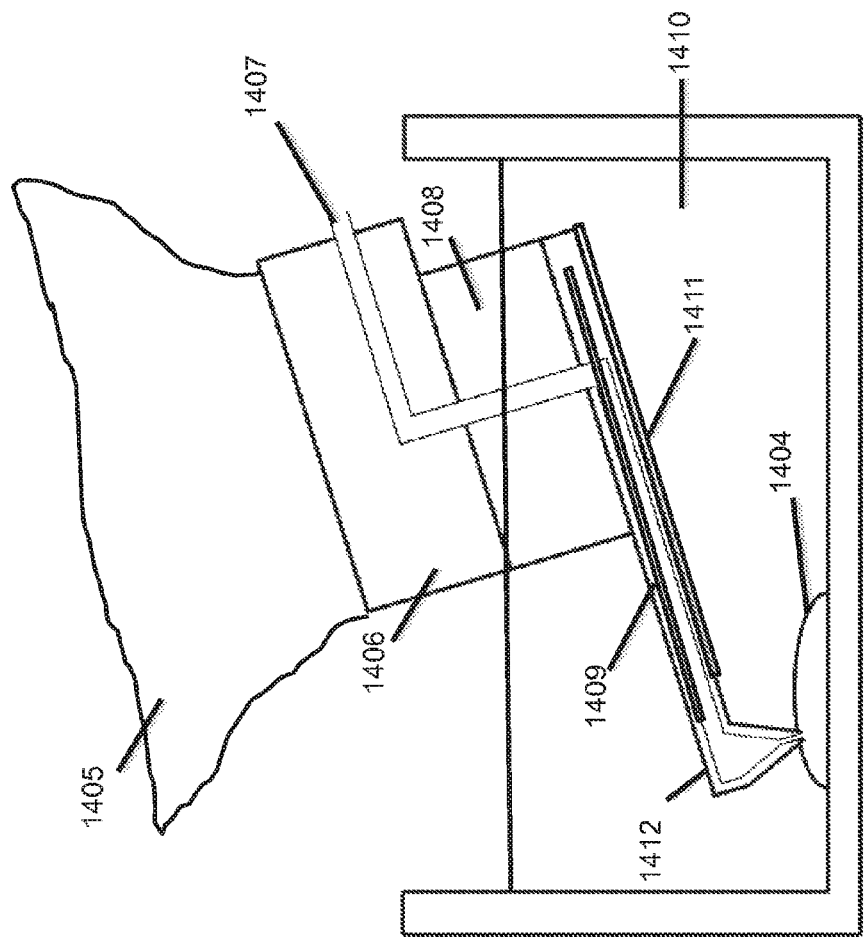
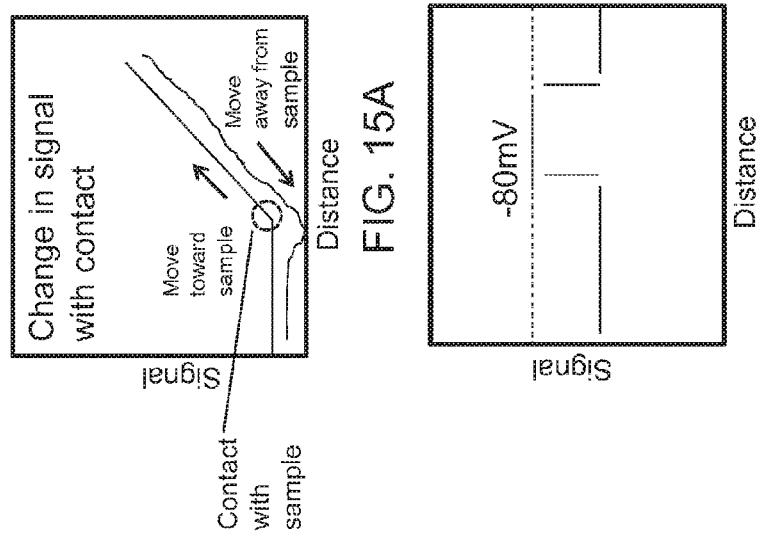

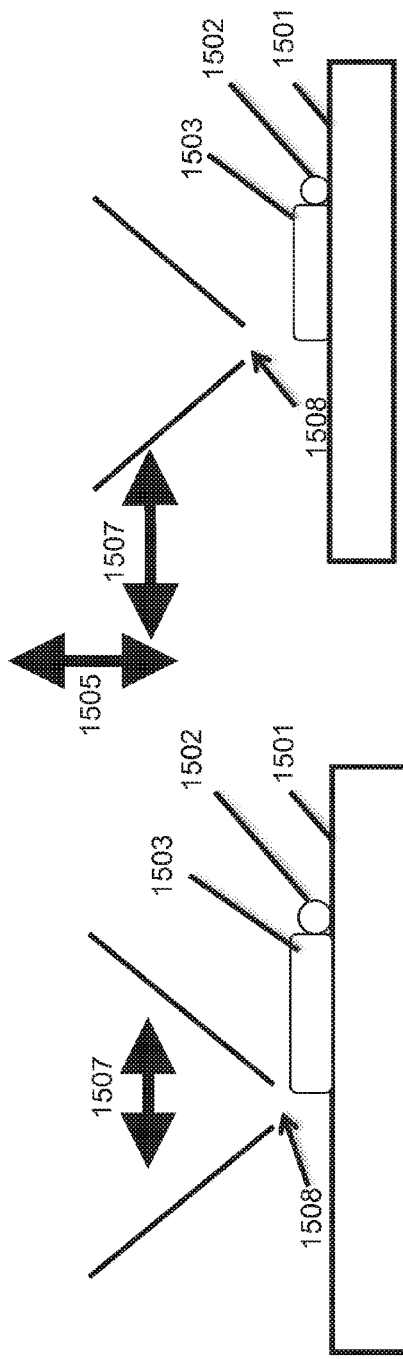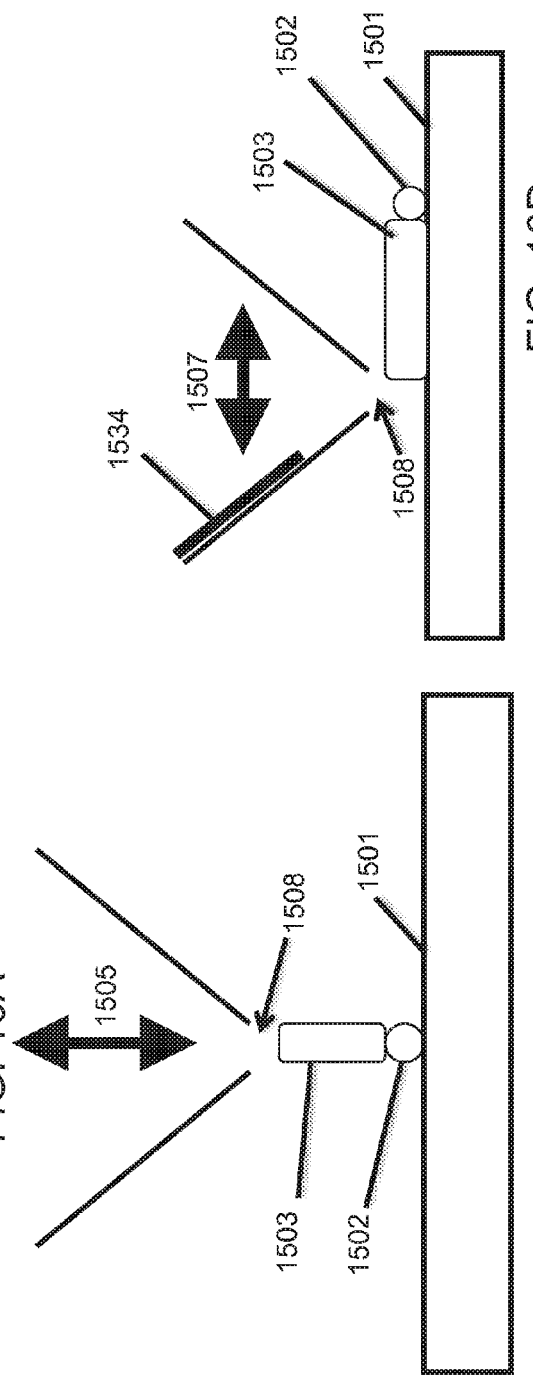

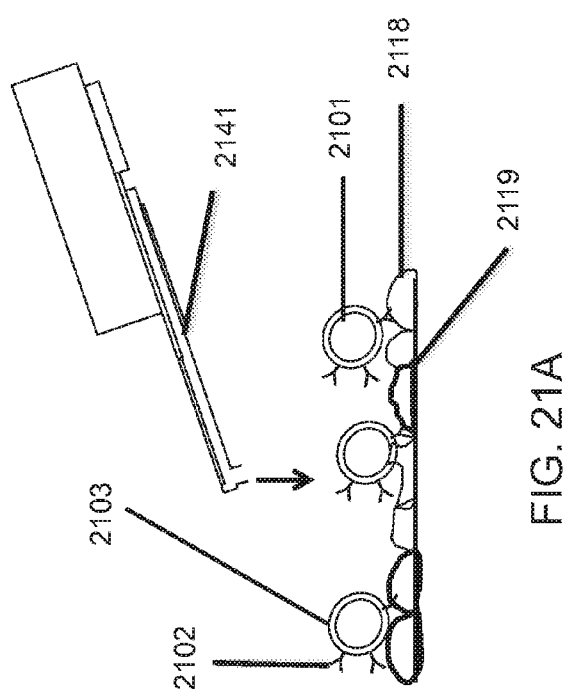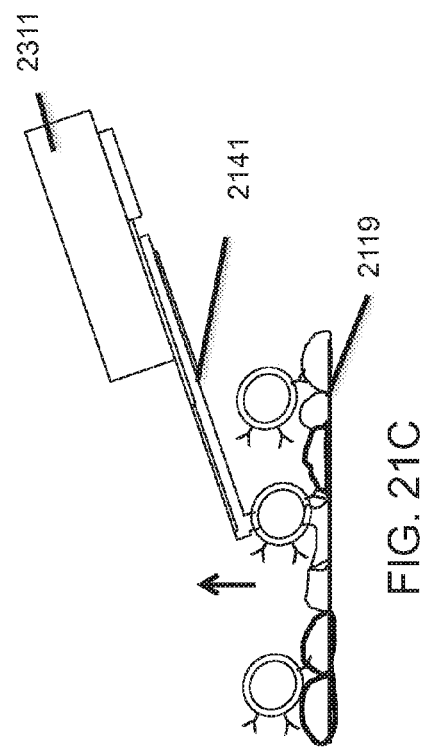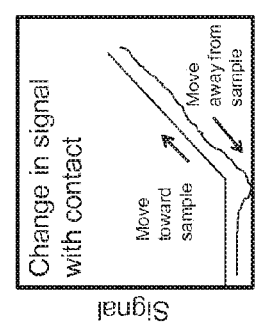
FIG. 21A
FIG. 21B
FIG. 21C

POLYMERIC MICRO-ARM APPARATUS AND METHOD TO USE THE SAME

CROSS-REFERENCE TO RELATED APPLICATIONS

This application is a continuation-in-part of application Ser. No. 13/099,351, filed May 2, 2011, which claims the benefit of U.S. Provisional Application 61/330,362 filed May 2, 2010, both of which are incorporated by reference in their entirety.

FIELD OF THE INVENTION

The present disclosure relates to micro electro-mechanical systems (MEMS). More particularly, the disclosure discusses polymeric MEMS and their methods of use.

BACKGROUND OF THE INVENTION

Glass micropipettes are regularly used to in biological applications such as patch clamping, extracting or delivering materials to cells, or extracting cells.

BRIEF SUMMARY OF THE INVENTION

The present disclosure discusses a polymeric micro-arm apparatus and method to use the same. The apparatus comprises: an elongated hollow polymeric structure with a distal end and a proximal end; an opening at the distal end; a substrate attached to the polymeric structure; means to move the polymeric structure; means to measure the polymeric structure movement; a pumping and vacuum device attached to the proximal end; an element embedded in the polymeric structure, wherein the element is configured to detect when the polymeric structure contacts an object and measure the pressure that the object exerts upon the polymeric structure.

The elongated hollow structure has a length which is substantially greater than its diameter.

The opening at the distal end is preferably perpendicular to the structure length. However, this perpendicularity is not necessary.

Means to move the structure can be any device which is capable of moving the structure in a controlled manner. In one embodiment, the structure can only be moved in the X-axis. In another embodiment, the structure can be moved in the X-axis and Y-axis. In another embodiment, the structure can be moved in the X-Axis, Y-axis, and Z-axis.

Means to measure the structure movement can be any measurement device.

The pumping and vacuum device enables the polymeric structure to expel or suction a gas or liquid.

In a separate embodiment, the apparatus further comprises one or more additional elements embedded in the polymeric structure. The additional elements can measure temperature, current, voltage, or the like.

In a separate embodiment, the apparatus further comprises a heater near the opening, at the opening, or inside the arm.

The polymeric structure material of construction can be SU-8, polyimide, silicone, parylene, or the like.

In a separate embodiment, the means to measure the structure movement is monitored with an external electrical measurement device (such as a multi-meter, voltmeter, source meter, resistance meter). The external electrical measurement device measures resistance, current, voltage, or some other electrical change.

The means to measure structure movement can be a piezoresistive element, piezoelectric element, elastoresistive element, conductive polymer element, metal thin film element (such as gold), doped silicon element, metal oxide element (such as a gold oxide), or the like.

The substrate material of construction can be silicon, silicon with a thin layer of oxide, silicon nitride, glass, SU-8, part of a printed circuit board (pcb), a polymer, a combination of the aforementioned, or the like.

In a separate embodiment, the substrate further comprises electrical pads.

In a separate embodiment, the substrate further comprises fluidic tubes.

Fabrication methods for the apparatus are further described in the detailed description and are also incorporated into the summary by reference.

The scope of the invention is defined by the claims, which are incorporated into this section by reference. A more complete understanding of embodiments on the present disclosure will be afforded to those skilled in the art, as well as the realization of additional advantages thereof, by consideration of the following detailed description of one or more embodiments. Reference will be made to the appended sheets of drawings that will first be described briefly.

The following detailed description of the invention is merely exemplary in nature and is not intended to limit the invention or the application and uses of the invention. Furthermore, there is no intention to be bound by any theory presented in the preceding background of the invention or the following detailed description of the invention.

BRIEF DESCRIPTION OF THE DRAWINGS

FIG. 3 shows a specialized AFM probe on a microfluidic chip.

FIG. 10 shows various methods that the apparatus can used for.

FIGS. 15A-15C show the arrangement for patch-clamping and micro-injections.

FIGS. 16A-16D illustrate fluidic delivery of a gas or a gas mixture or a liquid or a liquid mixture.

FIGS. 21A-21C illustrate an application of the hollow cantilever probe.

DETAILED DESCRIPTION OF THE INVENTION

The limits of glass micropipettes and other glass devices is that they are not soft enough and do not have a mechanism to detect the degree of contact, which can result in damaging tested material. Hence, the present disclosure discusses a polymeric micropipette which overcomes these limitations.

Figure 1A:
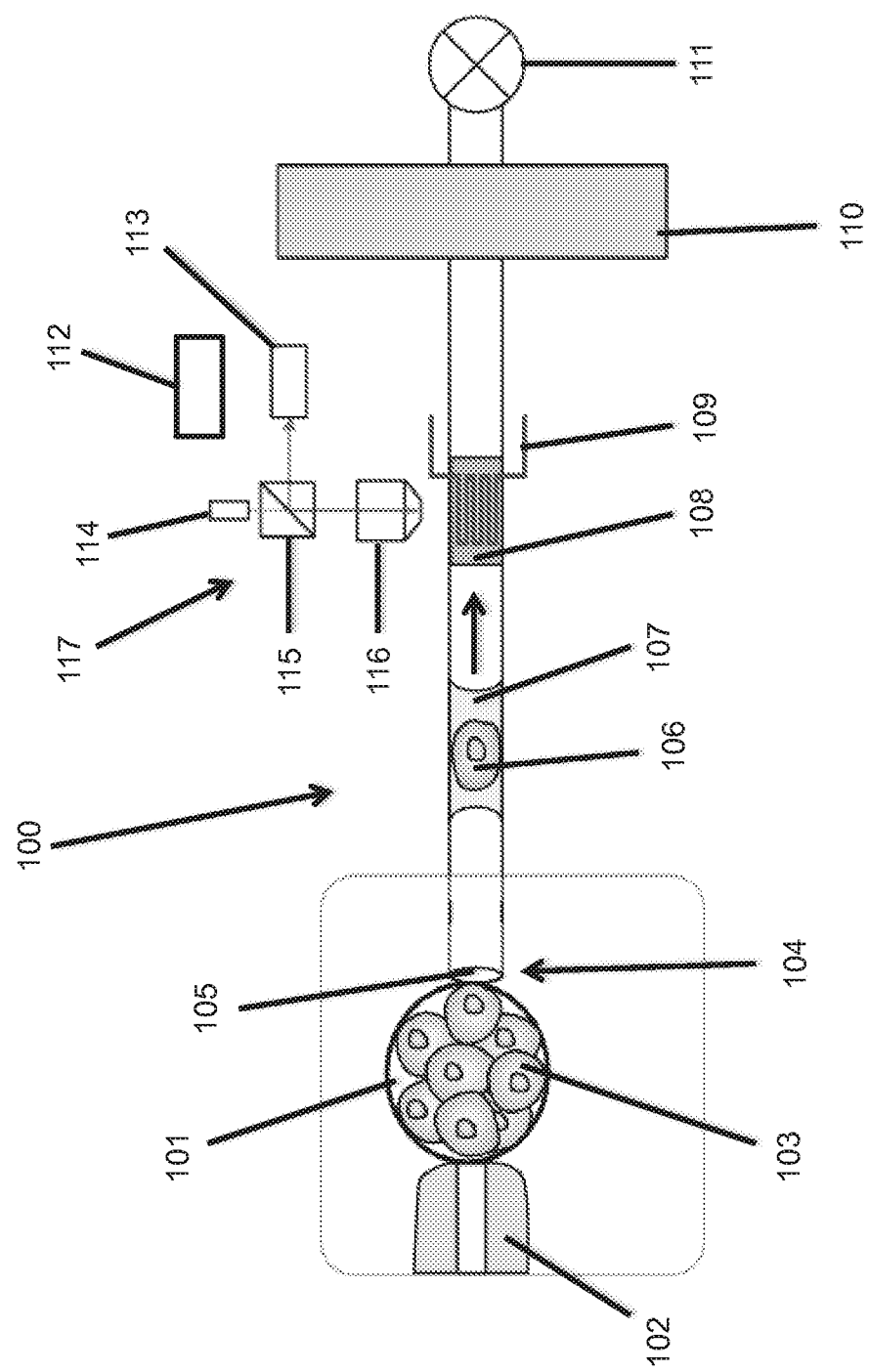
FIG. 1A shows a 'lab-on-a-pipette' device.

Referring now to the drawings, more particularly to FIG. 1A, which shows a 'lab-on-a-pipette' device 100. In FIG. 1A: an IVF petri dish 101 contains 6-8 cell embryos 103 held by a holding pipette 102. A micro aspiration tip 104 with a 40 μm diameter opening 105 extracts an encapsulated single cell 106. The cell 106 is encapsulated by a 300 pL plug 107. The device 100 contains embedded lysis and PCR reagents (lypholized) 108, and a microheater 109 for PCR cycling. The pipette 102 is controlled by a micromanipulator 110. A precision suction pump 111 is also used. Also shown is a detection system 117 comprising a LIF Detector 112 (Off Chip), PMT 113, Laser 114, Filter Cube 115, and Objective lens 116.

In one embodiment the microaspiration tip extracts and encapsulate a cell into an ultra-low volume plug. The microfluidic analysis module with embedded lyophilized reagents performs cell lysis, PCR amplification, and real time fluorescence analysis. Micro-machined aspiration tips are coupled directly to sensitive microfluidic analysis modules. The device addresses major limitations of the current PGD procedures by being able to analyze small amounts of DNA, eliminating fluid transfers which cause contamination (the cell is transferred directly for analysis), reducing analysis time, and reducing costs (less people involved in genetic diagnosis, reduced procedures and time, elimination of expensive hardware).

Figure 1B:
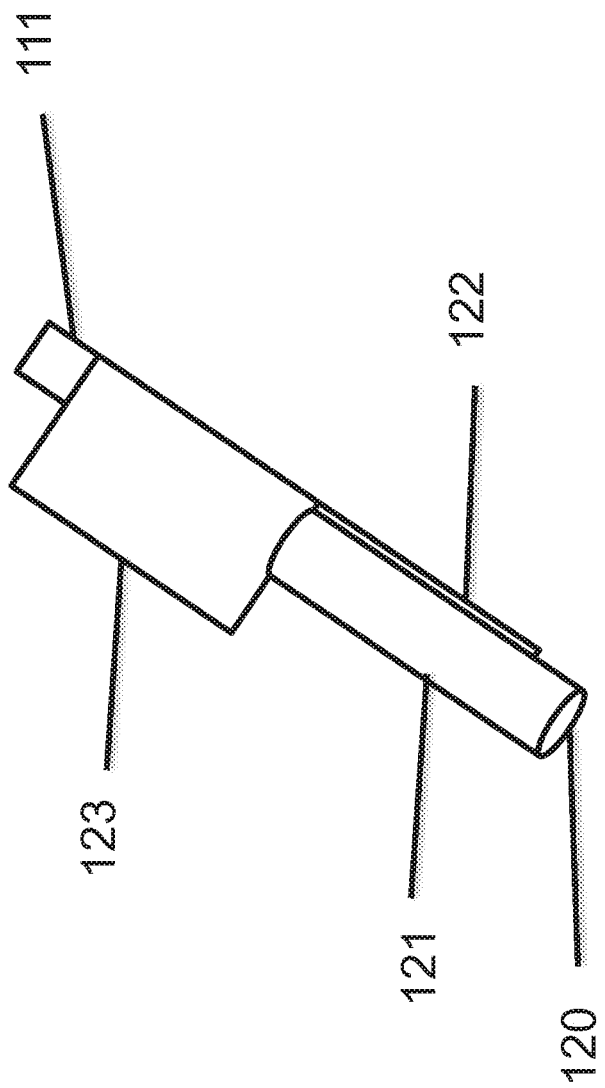
FIG. 1B shows a generalized lab-on-a-pipette' device.

FIG. 1B shows a more generalized version of the device that includes a tip with an opening 120 and a microarm 121. The opening 120 ranges from a few nanometers to a few microns in diameter. For example the opening 120 could be 1 micron in diameter. The device includes a sensing and/or actuating element 122. For example, element 122 is a piezoelectric or piezoresistive element to sense movement or displacement of the device. In one embodiment these elements are added to the device on each side to sense up and down movement as well as left and right movement. In one embodiment these elements are used to move (actuate) the device. For example a piezoelectric element is used to move the device. In one embodiment a sensing element is used to image a surface by measuring the displacement of the device in the Z-axis (up and down, out of place direction). In another embodiment, a sensing element is used to measure the elasticity (the stiffness) of a sample like a cell to determine how hard or how soft it is. In one embodiment the analysis unit 123 (or lab-on-chip) attached to the device includes any of the following processes/methods/devices/techniques by themselves or in combination: a fluorescent in situ hybridization (FISH), a polymerase chain reaction (PCR) amplification, a whole genome amplification, a comparative genomic hybridization, a pre-implantation genetic diagnosis, micro-cantilever based detection, cell lysis, and real time fluorescence analysis. In another embodiment the analysis unit 123 includes any other type of process/method/device/technique that is used to analyze a biological sample such as a cell, part of a cell, protein, DNA, organelle etc. In one embodiment pumping 111 to draw the analytes in the microfluidic analysis system is achieved with a simple syringe operated manually, or with a micro-pump (i.e. a small micromachined pump of dimension comparable to the analysis unit), or with any other type of pumping system capable to producing sufficient suction to draw the analytes in the microfluidic system. The device of FIG. 1A or 1B is powered by any means including but not limited to: batteries, AC power supply etc.

Figure 2:
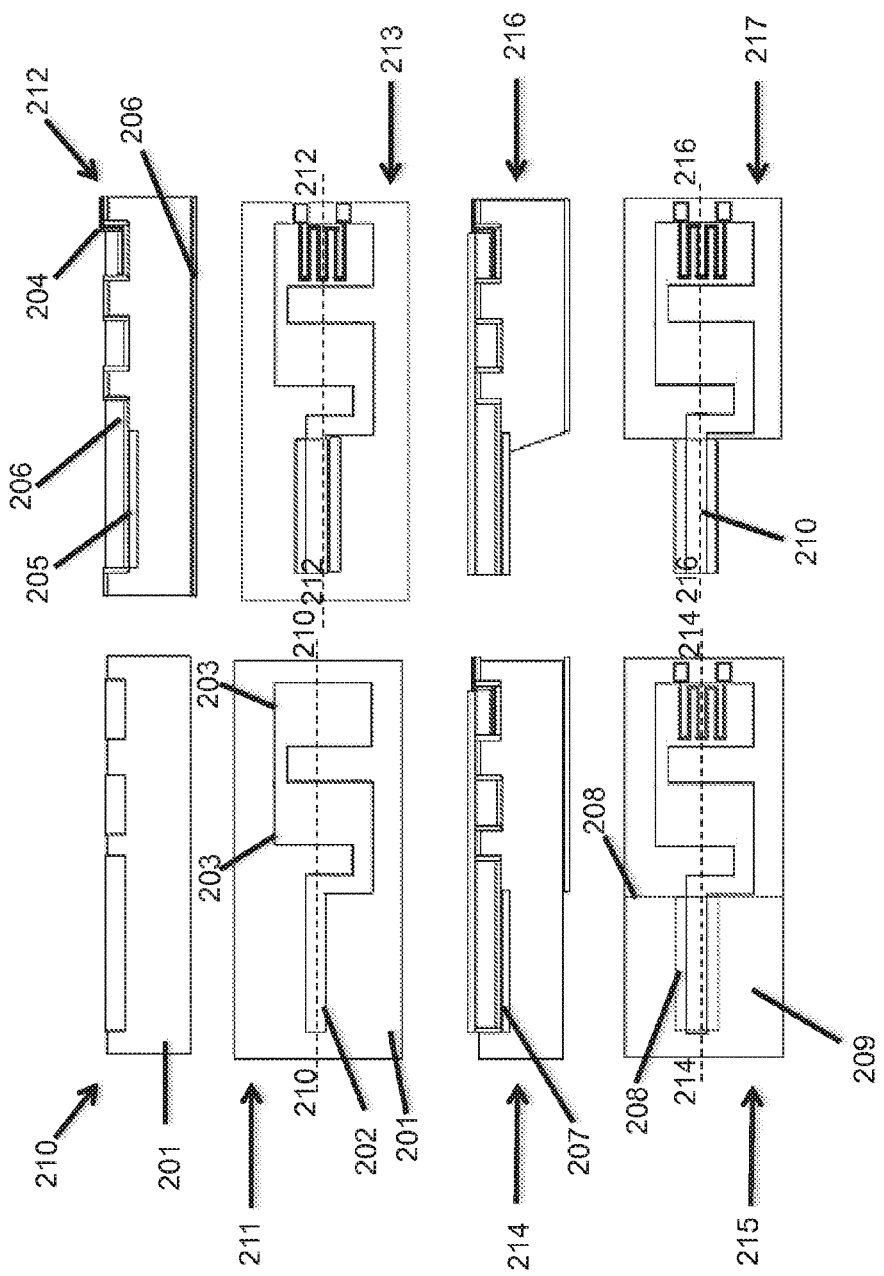
FIG. 2 shows the microfabrication process for a chip with an integrated sampling probe.

FIG. 2 shows the microfabrication process for a chip with an integrated sampling probe. Both top views and side views are shown. 210 (cross-section) and 211 (top) forming trenches and cavities on silicon using deep RIE (silicon substrate 201, trench 202 for sampling, channels 203 for microfluidic components); 212(cross-section) and 213(top) selectively and heavily doping the sampling probe region on the silicon substrate, growing a thermal oxide layer, and then sputtering and lift-off of platinum as heating and temperature monitoring device (sputtered platinum 204, P+ doped silicon 205, thin thermal oxide 206); 214(cross-section) and 215(top)) filling the trenches and cavities with low-evaporation oil or photoresist as sacrificial material (sacrificial oil/photoresist 207), depositing and patterning a thick layer of parylene on top (thick parylene 208) of the thermal oxide and the oil/photoresist to seal the channels and microfluidic chambers, and then patterning the oxide on the front and back side of the silicon substrate in buffered HF acid (BHF); 216(cross-section) and 217(top) releasing the sampling probe in TMAH or EDP etchant with p+ doped region for etching stop, etching oxide at the tip of the sampling probe in BHF to open the channel, and draining or dissolving the sacrificial oil/photoresist (exposed silicon 209, released probe 210). In one embodiment another PDMS layer is casted on top of the parylene layer for additional structural strength in the microfluidic device region.

Microscopic pores in the lyophilized reagents obtained in the freeze drying process permit the flow of gas when suction is applied to the device by the precision syringe pump. The suction pulls the encapsulated cell towards the lyophilized reagents, and upon contact, reconstitutes the PCR and lysis reagents with the cell plug. At this time, the cell becomes lysed and ready to undergo PCR cycling. Thermal cycling for PCR will require two high temperature steps for assisting in cell lysis, followed by 20-30 cycles of annealing and extension steps as needed for amplification. Detection of PCR requires a standard Laser induced fluorescence detector.

FIG. 3 shows a specialized AFM probe on a microfluidic chip. This device combines scanning probe microscopy (SPM) with CE to investigate single cell and nucleus biomolecules. A micromachined (MEMS) nanoscale fluidic scanning probe and scanning and analysis system with ability for imaging (morphology mapping with nanometer resolution) and low abundance biomolecule measurements of cells is claimed. The probe allows the visualization of subcellular structure. The same probe functions as a nanoscale pipette allowing the extraction of biomolecular contents of individual nucleus or other organelles of a cell and their subsequent manipulation, labeling, separation, and quantification without the need for lysing. DNA can be extract from the nucleus of a cell without lysing. This tool permits quantitative and real time observation and brings new levels of understanding of the molecular physiology of cells, as well as the manner in which this physiology is affected by disease, pharmacologic agents, development, and other factors, overcoming limitations of other techniques such as having to remove the cell from its environment and surrounding cells for analysis. FIG. 3 shows a nucleus 301 in the cytoplasm 302. The cell membrane 303 is penetrated by a 304 nano probe 304 with hollow tip 308. The material is extracted and flows through the probe chip 305 via a fluidic transport channel 306. The probe is held by the 307 probe holder with fluidic channel. A laser light 330 for probe movement tracking is reflected on the cantilever's backside. Alternatively an embedded element such as a thin film of metal is used to track the movement of the cantilever. The probe can be controlled with a AFM XYZ piezo 331 for probe movement. A glass slide (substrate) 333 and below inverted microscope with florescent can be used to view the cell and probe. The probe and cell are in a buffer solution 334.

This highly sensitive detection system is used to measure the concentration of low abundance biomolecules such as DNA (<1000 molecules/cell) inside the nucleus of a single cell. A cantilever hollow probe with a nanometer size opening at the sharp tip is integrated with a capillary electrophoresis (CE) system. The probe operates in aqueous environments and includes a microfluidic channel through the cantilever. The probe allows for extraction of biomolecules directly from an organelle through a sub-100 nm size hole on the probe tip into the microfluidic channel. Using an atomic force microscope (AFM or scanning probe microscope—SPM) contact can be achieved with direct control of applied forces reducing the potential damage to the cell or the nucleus. High resolution imaging and sub-cellular elastography can also be achieved. This system can provide sensitive, inexpensive, fast detection of low abundance biomolecules for cellular analysis, cancer biomarker detection, and drug development.

Figure 4A:
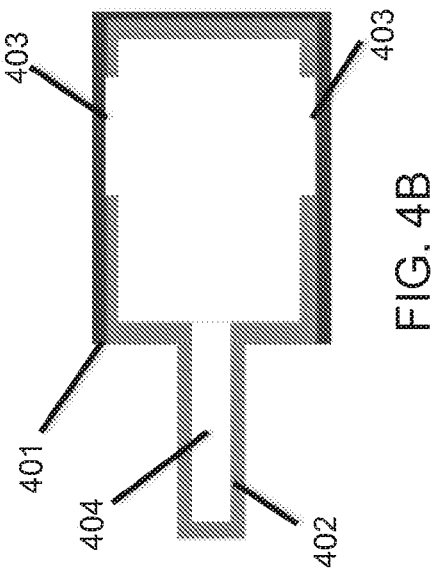
FIGS. 4A-4D show an embodiment of a polymeric microarm apparatus.
Figure 4B:
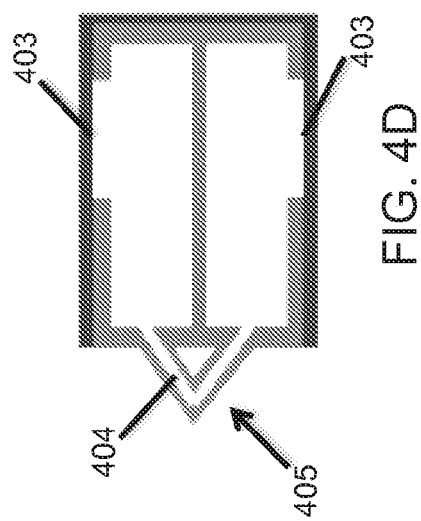
Figure 4C:
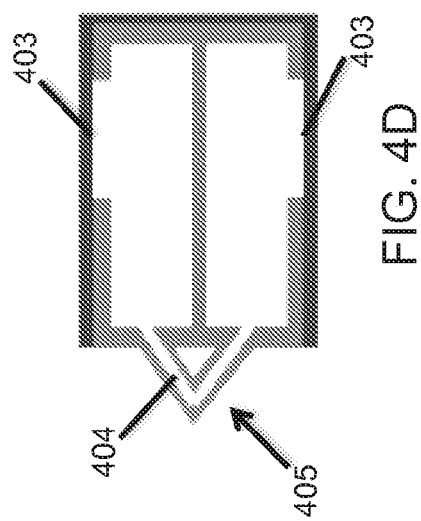
Figure 4D:
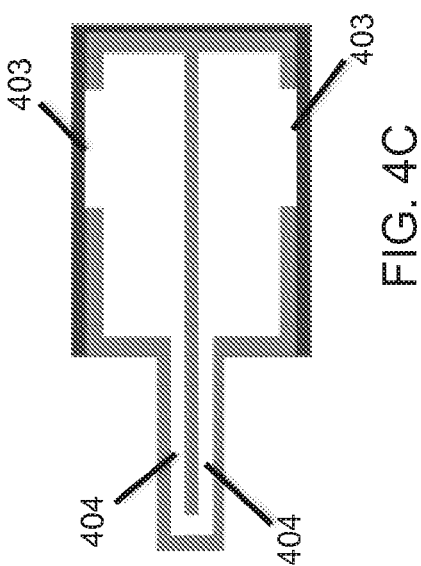
Figure 8:
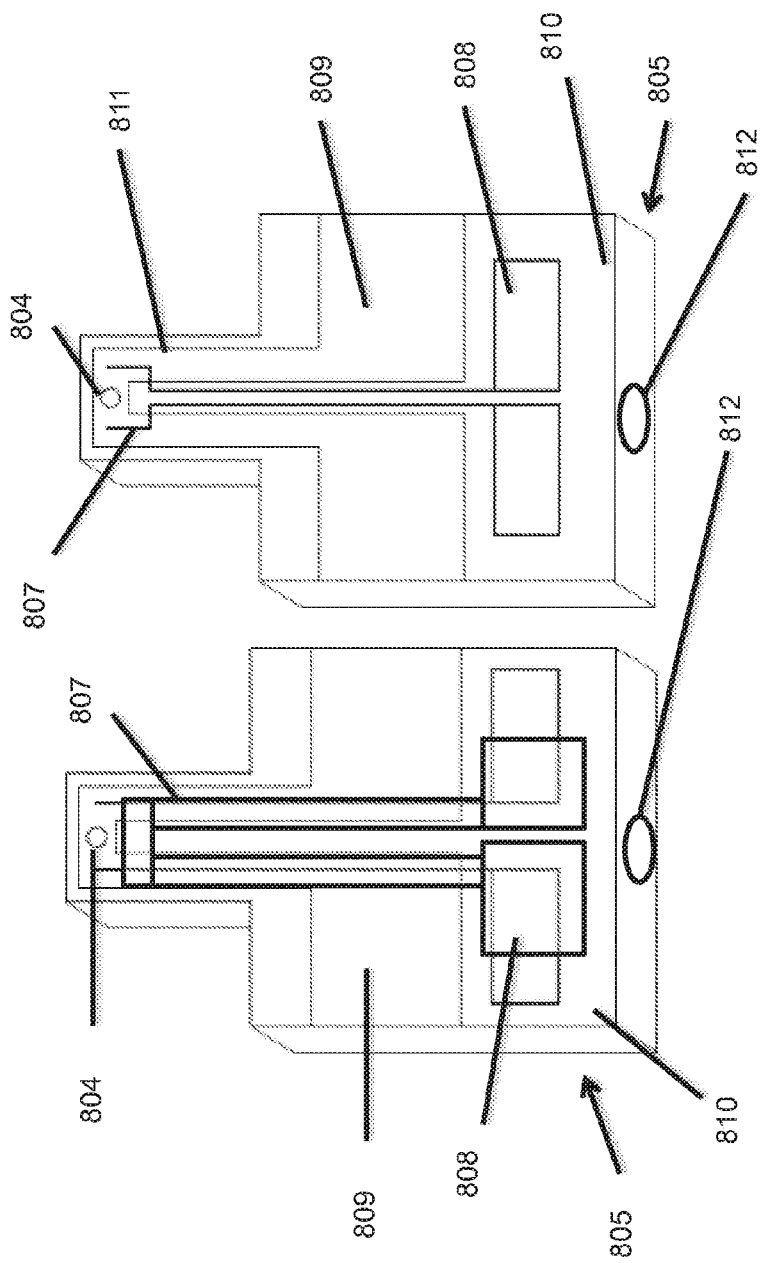
FIG. 8 illustrates lines for displacement sensing.

FIGS. 4A-4D, show embodiments of the polymeric micro-arm apparatus. FIG. 4A is a side-view and FIGS. 4B-4D are bottom views. The entire cantilever structure is made of a polymer like parylene or polyimide and the substrate for mounting the device to AFM is made of SU-8 or silicon. There are multiple shapes and channels. FIG. 8 shows some of the designs. The size of the rectangular shape cantilever is about 100-400 µm wide and 200-1000 µm long; the size of the V-shape cantilever is about 100-150 µm wide. Elements show are Su-8 die 401, parylene 402, port 403, channel 404, and V-shaped cantilever 405. These examples are only indicative of a size, the sizes vary.

Figure 5:
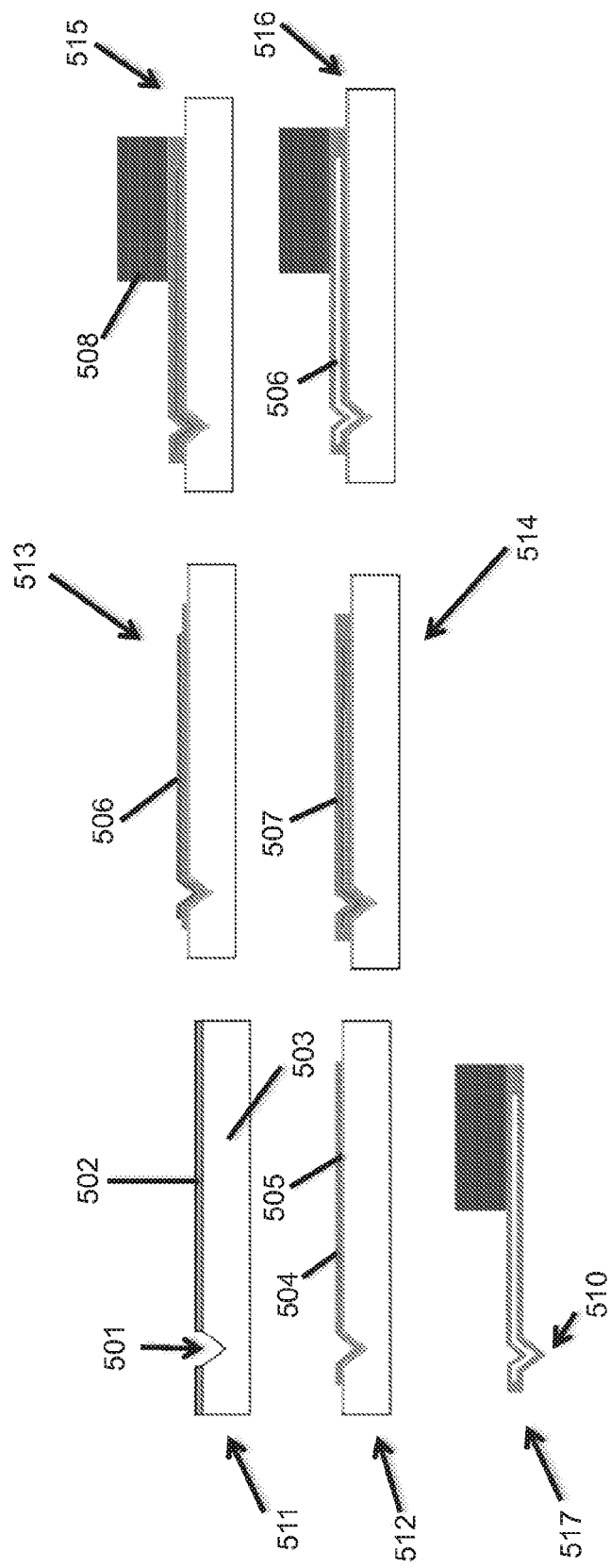
FIG. 5 illustrates an additional micro-fabrication process for fabrication the device.

FIG. 5 shows a fabrication process. A nanoscale size hole at the tip is made by focused ion beam (FIB) at the tip. The fabrication processes involves: step 511 forming a notch on silicon and growing oxide for oxide sharpening; step 512 deposition of titanium, which acts as a sacrificial layer and the first layer of parylene; deposition of secondary sacrificial layer; step 514 deposition of a second layer of parylene; step 515 deposition of handling chip made of SU-8; step 516 removal of bottom sacrificial layer and of sacrificial layer in the channel; step 517 FIB to make hole and metal deposition on the back-side. Enhanced designs include micro pillar arrays to support the large diaphragm or long walls to isolate the channel. SiO2 501 tip is formed and sharpened and silicon oxide 502 is grown on the Si substrate 503. Ti 504 is deposited as a sacrificial layer and on top of polymer 505 to form the first part of the device, then a sacrificial layer 506 is deposited that will later on be removed to form the hollow part of the device and another layer of polymer 507 is patterned and deposited to form the top part of the device. Su-8 508 is posited to form the body of the chip. Then sacrificial layer 506 is removed. FIB 510 is used to make a hole and metal is deposited on the backside for reflectance.

An alternative fabrication process entails attaching a commercially available device on a substrate and fabricating the microfluidic chip described previously on the substrate. Yet another fabrication process includes bonding of two silicon wafers or one silicon and one glass wafer, where the device is included on the design and one wafer includes the micro-fluidic chip.

In another embodiment, the micro-fluidic device includes a fluorescence in-situ hybridization (FISH) module. The device is used for low-copy-number biomolecule (<1000 molecules/cell) detection of any type of biomolecule including proteins.

In one embodiment the device is used with a scanning system. For example, a motorized or a piezoelectric stage or a combination may be used to control and move the device and/or the sample. In one embodiment the device is used with an atomic force microscope (AFM) or scanning probe microscope (SPM). The device can be fabricated using conventional cantilever fabrication techniques and it includes a hollow area within the cantilever with an opening on one side at the tip and on the other side to the microfluidic analysis system.

In one embodiment the device includes an integrated heater at the end of it. The heater is used for penetrating the zona pellucid or other purposes. An integrated heater is included in other parts of the pipette or the fluidic system to create a fluidic flow.

The device is used to detect for example disorders like cystic fibrosis, Charcot-Marie-Tooth neuropathy, haemophilia A, breast cancer, lung cancer, prostate cancer and other types of cancer. It is used to detect and measure the concentration of various analytes in blood such as concretion of drugs like heparin. The device may be used for in serum-based diagnosis to extract blood and isolate, detect, amplify, and analyze specific cells such as circulating tumor cells (CTCs) that circulate in the bloodstream. The device is used to analyze cell membrane, organelles, and ion channels on the membrane of the cell.

In one embodiment the microfluidic analysis module includes a technology for the detection low abundance biomolecules inside the fluidic chamber (also referred to as the fluidic module) such as an array of microcantilevers with embedded piezoresistive sensors in a microfluidic chip. Micromachined cantilever arrays coated with specific antibodies include embedded piezoresistive sensors to identify an analyte by measuring the change of resistance of the sensor caused by the bending of the cantilevers. The chemomechanical bending of the cantilever is mainly due to the surface stress generated from analyte adsorption or binding with the coated receptors. The cantilevers is coated with the desired receptors to bind proteins, peptides, or micro RNAs. Several additions and aspects include: 1) use of polymer (like parylene) to fabricate the cantilevers, 2) reduction of cantilever size to micron and submicron dimensions, 3) ultra thin metallic piezoresistive films increase sensitivity and eliminate the need of the atomic force microscopy optical detection system, 4) address non-specific binding and noise using a combination of strategies including a reference cantilever. The sensing mechanism of the cantilever is based on either stress/strain change (in defection) or mass/frequency change (in resonant mode). This enables a portable integrated system. Previously cantilevers could not be used in the presence of serum proteins because the signal from non-specific adsorption of serum proteins was greater than the signal from the biochemical of interest. Superhydrophobic textures designed on the cantilever surfaces and chemical modification can help prevent non-specific adsorption. In addition, other cantilevers use laser detection which does not function well in serum blood. High sensitivity can be achieved by using polymer like parylene cantilevers advancing the sensing limits to detect low abundance biomolecules. The device can be scaled to measure concentrations of different analytes by having a number of cantilevers in an array or a number of wells each with a cantilever coated with relevant antibodies. Operation in the presence of ambient proteins and absence of biofouling means the devices will not require prior separation of proteins. The analysis time is on the order of several minutes and is determined by the flow rate of the serum over the cantilever probes for close contact and the diffusion time of the proteins to reach the binding reagents. Compared with ELISA that requires labeling using an enzyme to elicit a chromogenic or fluorogenic or electrochemical signal, this technique is rapid and detection can be done at any location. The binding process between the antibodies and antigens can be monitored real-time. A 20×20 array of cantilevers (400 cantilevers) can easily fit in 10 mm×10 mm area while all of the electronic components fit on a low power chip.

In one embodiment the claimed integrated device provides "sample-to-answer" single cell genetic diagnosis for preimplantation genetic diagnosis (PGD) and other forms of single cell analysis (SCA). The device integrates a microaspiration tip with microfluidic analysis components to conduct in-situ, real-time single cell genetic diagnosis in a single device. The microaspiration tip extracts and encapsulates a cell into an ultra-low volume plug (<1 nL). The microfluidic analysis module with embedded lyophilized reagents will perform cell lysis, PCR amplification, and optionally real time fluorescence analysis. This device couples micromachined aspiration tips directly to sensitive microfluidic analysis modules, providing single cell sampling and isolation. The device eliminates fluid transfers which cause contamination, reducing analysis time, and reducing costs.

The apparatus combines microfluidic diagnostics with micromachined hollow tips in an integrated, automated system for in-situ diagnosis. The apparatus completes an analysis much faster because there is no need for instance to transfer the cells to different tubes and ship the cells to a different location for analysis. In addition, amplification can be done much faster, embedded micro-heaters can heat to 100° C. in less than 10 seconds, reducing the time that it takes to complete 30 cycles to a couple of minutes from the current 10 minutes. The smaller fluid volumes in the form of plug handled by the micropipette and microfluidic apparatus increase the effective concentration and provide better amplification with improved results and better chances of measuring single gene mutations.

In one embodiment the fluidic system consists of a commercially available precision suction pump and micro connecting tubes that will attach to the apparatus. Other types of micro-pumps can be used. These may be integrated with the apparatus. A scanning system can be modified and adapted for microfluidic experimentation. In one embodiment the system is equipped with a piezo scanner with a maximum XYZ scan range of 100 um×100 um×100 um and 1 nm resolution and a motorized scanner with XYZ 25 mm×25 mm×25 mm with 5 micron resolution. In the same embodiment peripheral devices include an inverted optical microscope, a CCD camera, and a signal access module, which can access most real-time signals inside the system. The tip of the apparatus (also called the device) can be placed on a coverslip or a micro-well that contains the cells. Using a micromanipulator, the apparatus can be guided over a cell. Suction can be applied to extract the cell from the coverslip into the apparatus.

Reagents for cell lysis and gene-specific primers for TAQMan PCR can be purchased. For example, TAQMan probes embedded into the lyophilized reagents can bind to genes in question, resulting in increased fluorescence if the matched gene sequence is present. The reagents can be combined appropriately, and pumped as a plug into the apparatus, and lyophilized on chip. The process of lyophilization (freeze drying) of biomolecules has been extensively studied, and the effect of process parameters are well understood. Proteins and reagents have been lyophilized on chip using a freeze drying process. Lysis reagents and PCR reagents can be combined together without adverse effects on the PCR reagent. The lyophilized reagents may occupy a 300-1000 μm length within the apparatus, above the microheaters. Alternatively, the reagents can be simply dried on the chip. This has been used successfully for RT-PCR amplification with RNA polymerase and other bioactive molecules.

The microheater can be formed by thin-film platinum and can also be used for temperature measurement as an RTD by monitoring the resistance change. The thermal cycling capabilities of microheater are characterized using an infrared microscope and microthermocouples. The apparatus provides programmable temperatures between 30 and 100° C., and have accuracy of 1° C., and thermal time constants <500 ms. PCR cycling can also be performed using an external laser. IR lasers are available with several watts power, and can bring their illuminated region to >100° C., well higher than what is needed for PCR cycling.

Microscopic pores in the lyophilized reagents obtained in the freeze drying process permit the flow of gas when suction is applied to the apparatus by the precision syringe pump. The suction pulls the encapsulated cell towards the lyophilized reagents, and upon contact, will reconstitute the PCR and lysis reagents with the cell plug. At this time, the cell will become lysed and ready to undergo PCR cycling. Thermal cycling for PCR will require two high temperature steps for assisting in cell lysis, followed by 20-30 cycles of annealing and extension steps as needed for amplification The lyophilized reagents can also be placed in a small cavity outside the primary channel.

Detection of PCR requires a standard laser induced fluorescence detector. A low cost 405 nm laser diode which provides up to 50 mW optical power can be used. The dichroic mirror, excitation, and emission filters will be obtained from commercially. Using a 40×objective, the light can be focused on the capillary where the reagents and microheater are located.

Cells can be aspirated into the apparatus in a 300 pL plug, reconstituted with the on-chip reagents, and thermally cycled. Typical temperature cycling conditions are 94° ° C., 55° ° C., and 72° C. for denaturing, annealing, and extension, respectively. Whole genome amplification reagents can be commercially obtained similarly generic intercalating dyes to measure the DNA concentrations during the PCR cycling can also be purchased from vendors. The reagents may include primers and probes for testing.

The apparatus comprises a positioning device (or otherwise called hollow cantilever or probe or hollow structure etc.) and a microfluidic component. The microfluidic component may be used for single cell analysis. A positioning device can be used to manipulate the apparatus in contact with an analyte. The sample can be a cell and the analytes can be cellular biomolecules such as DNA or proteins. The analyte can be a cell, an organelle, the membrane of a cell, or a channel on the membrane of a cell. The fluidic module may include temperature controlled chambers. The fluidic module may include an optical analysis chamber and chambers for mixing the sample with dried or liquid reagents. The apparatus may also have an element to control fluid motion such as a pump. The hollow structure may include an element for sensing movement or an element for moving the hollow structure. The elongated hollow structure may include a heater. The fluidic module may include components to perform cell lysis and polymerase chain reaction amplification. The fluidic module may include components to perform real time fluorescence analysis. In general this apparatus can be used as follows: positioning the hollow cantilever with an opening near an analyte, bringing the analyte through the opening into the channel, moving the analyte through the channel into a fluidic unit connected to the channel, performing processes to the analyte in the fluidic unit, and detecting the analyte. The analyte can be a single cell that is encapsulated in a liquid plug with analysis reagent, and the fluidic unit may include a lysis component to lyse the cell and a thermal cycling component to amplify certain predetermined macromolecules of the cell. The fluidic unit may include an analysis component to analyze and read the results using optical or electrochemical detection. The sample to be analyzed is a cell and the analytes are cellular biomolecules such as DNA or proteins, an organelle, the membrane of a cell, a channel on the membrane of a cell.

Figure 6B:
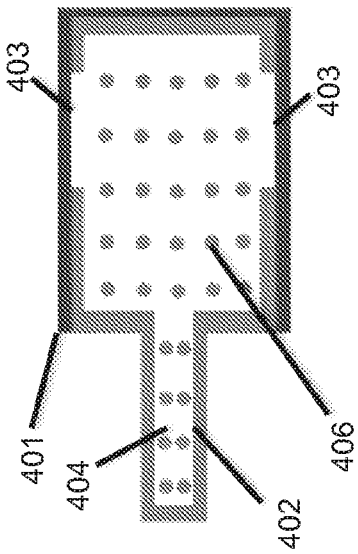
FIGS. 6A-6D illustrate hollow cantilever probe designs with pillars for supporting the cantilever's top and bottom layers.
Figure 6D:
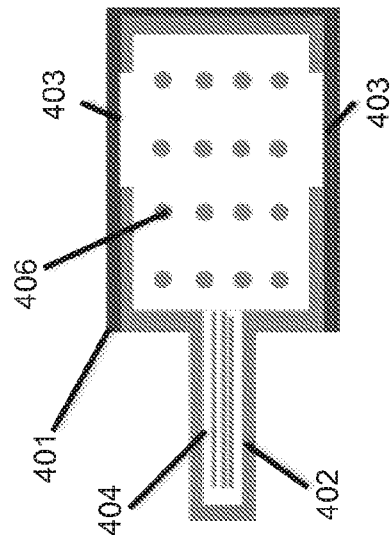
Figure 6A:
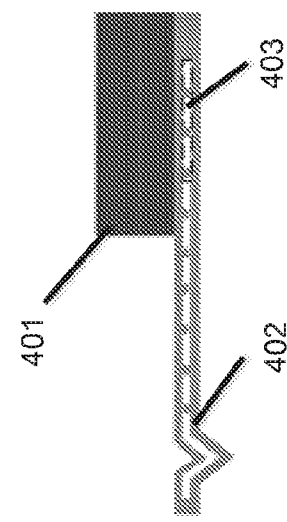
Figure 6C:
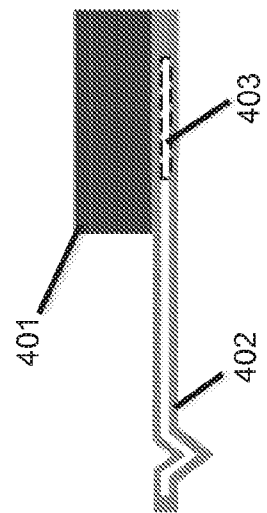

FIGS. 6A-6D illustrate hollow cantilever probe designs with pillars for supporting the cantilever's top and bottom layers. FIG. 6A is a side-view and FIGS. 6B-4D are bottom views. In these embodiments the cantilevers are made of a polymer such as parylene, polyimide, or other polymer. The tip is sharp although in other embodiments it has other shapes. Elements show are Su-8 die 401, parylene 402, port 403, channel 404, and pillar 406.

Figure 7:
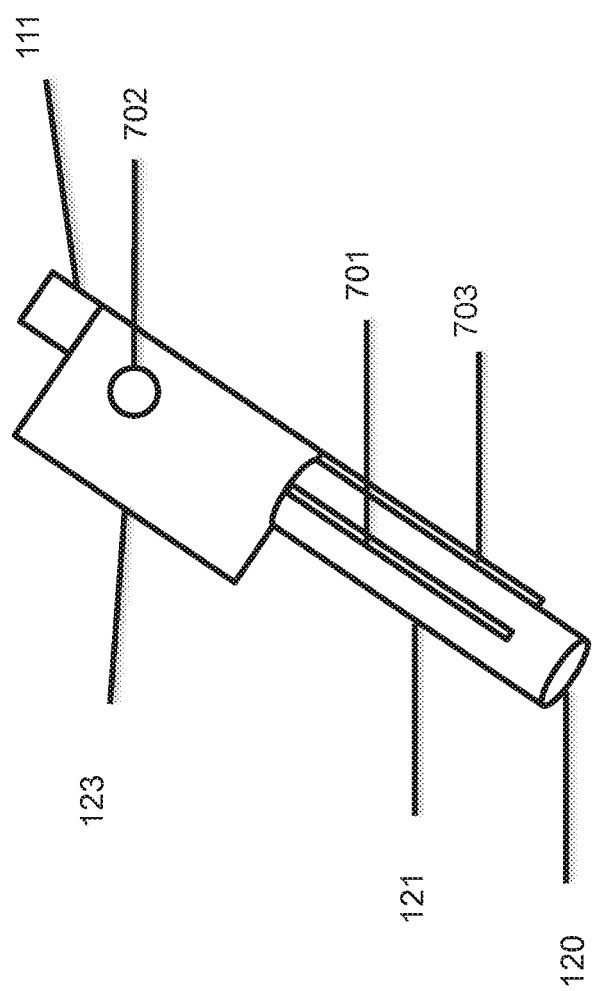
FIG. 7 illustrates an apparatus similar to FIG. 1B.

FIG. 7 illustrates an apparatus similar to FIG. 1B. However this apparatus has two sensing elements for sensing movement. One sensing element 701 and another element 703 are both on the same pipette cantilever. 702 is an opening for the tube connection. A tube connected from 702 is used for: pumping fluids in or out of the tip.

FIG. 8 illustrates lines for displacement sensing (top view) 805. Sensing elements are made of one of the following: piezoelectric material, piezo-resistive material, elasto-resitive material, organic conductors, piezo-resistive polymer, or other material that exhibits a change in electrical properties when bent or with change of shape. This apparatus can be modified for sensing contact like a robotic finger. The sensor runs from the body of the apparatus (also referred to as substrate) 810 to the pipette (cantilever) 811. The opening 804 is shown. Electrode 807 is shown with contact pads 808. This electrode 807 is used for a variety of purposes. In one embodiment, electrode 807 is used to measure ion channel current of a cell. In another embodiment, electrode 807 is used to induce a current to a biased substrate (to induce chemical reactions on the substrate for example). As seen, electrode 807 runs outside the fluidic chamber 809 and the fluidic cantilever 811 for the most part but in one part electrode 807 is in the fluidic cantilever 811 area. The fluidic chamber 809 and cantilever 811 are connected to an opening 804 on the cantilever 811 and an opening 812 on the body of the apparatus (substrate) 810. In another embodiment the substrate (the body of the apparatus) is a pcb (printed circuit board). The pipette (cantilever) is directly fabricated on the pcb. One skilled in the art can use a pcb as a substrate for other cantilever devices (and micro-fluidic devices) such as AFM, SPM, scanning thermal microscopy. Alternatively one can use a pcb as a substrate for neural probes or other type of pipettes such as patch clamps that require electrical contact. The benefit of using a PCB is that it includes electrical contact pads that thin films can be deposited on to establish contact with the apparatus thereby eliminating wirebonding. Leads can be designed to run far away to the other side of the cantilever where wires can be easily placed to include electrical contact for powering the electrodes and sensors and for measuring the signals. The fluidic section including an optional analysis or amplification unit are directly fabricated on the PCB. An alternative substrate material is glass or silicon or silicon oxide or silicon nitride or SU-8, or polymer or any other substrate that has been used in cantilever fabrication.

Figure 9:
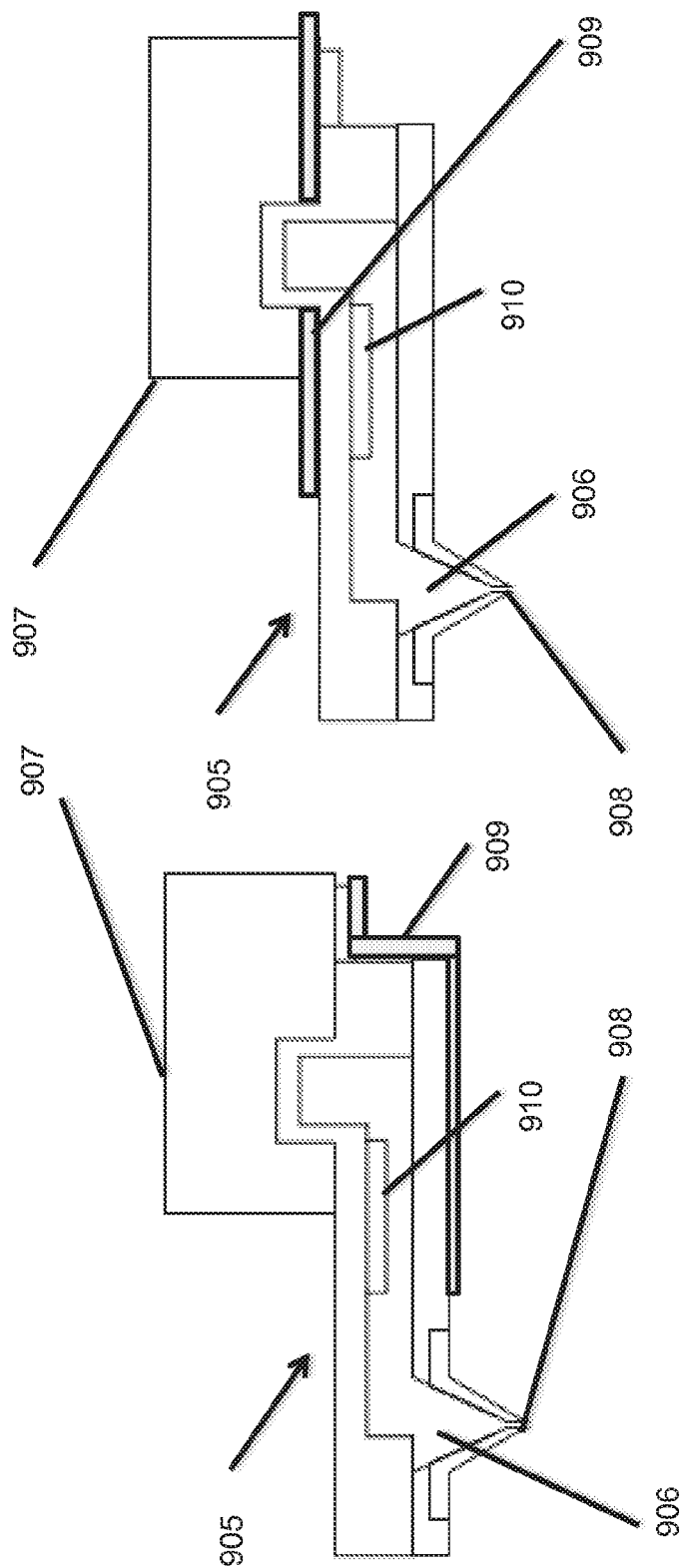
FIG. 9 illustrates the cross sectional view of the apparatus.

FIG. 9 illustrates the cross sectional view of the apparatus. The size of the rectangular shape cantilever 905 varies between 100-200 μm in width. The length varies from 150 μm to 500 μm. Typical micro-channel 906 dimensions are of 2 μm in height and 10 μm in width. The cantilever walls are made of polymer material such as polyimide or parylene or SU-8 or elastomers. For example, walls can have a thickness ranging from 100 nm to 100 μm. The substrate 907 for mounting the apparatus is made of Su-8 or silicon/silicon-oxide or other material as described above. The tip 908 is typically pyramid-shaped with a base of 10 μm×10 μm and height of 7 μm. A hole at the tip is made by focused ion beam (FIB). The hole can be controlled to 20 nm accuracy and size with FIB. In another embodiment other micro-fabrication techniques are used to make a hole. In other embodiments there is no tip, but there is an opening at the distal end of the pipette. The opening faces down or front. The sensing elements 909 reside at the bottom or the top of the cantilever (pipette). An electrode 910 is included inside the channel. All these dimensions vary per application. In one embodiment a heater is embedded. The heater is made of metal such as platinum or gold. The heater is also used as a thermometer. In one embodiment, the design of the heater/thermometer includes four wires/leads connecting at the distal end. In one embodiment, the heater/thermometer is calibrated using noise thermometry calibration. The heater is used for lysis or other applications. The main body (or substrate or chip) of the apparatus includes a fluidic channel (or chamber) connected on one side to the fluidic channel (or hollow cantilever's channel) of the pipette and on the other to micro-tubes (tubes) that are connected to an external pumping unit and other units for liquid transfer or extraction. In one embodiment, the micro-pumping unit is embedded onto the main body of the apparatus.

Figure 10:
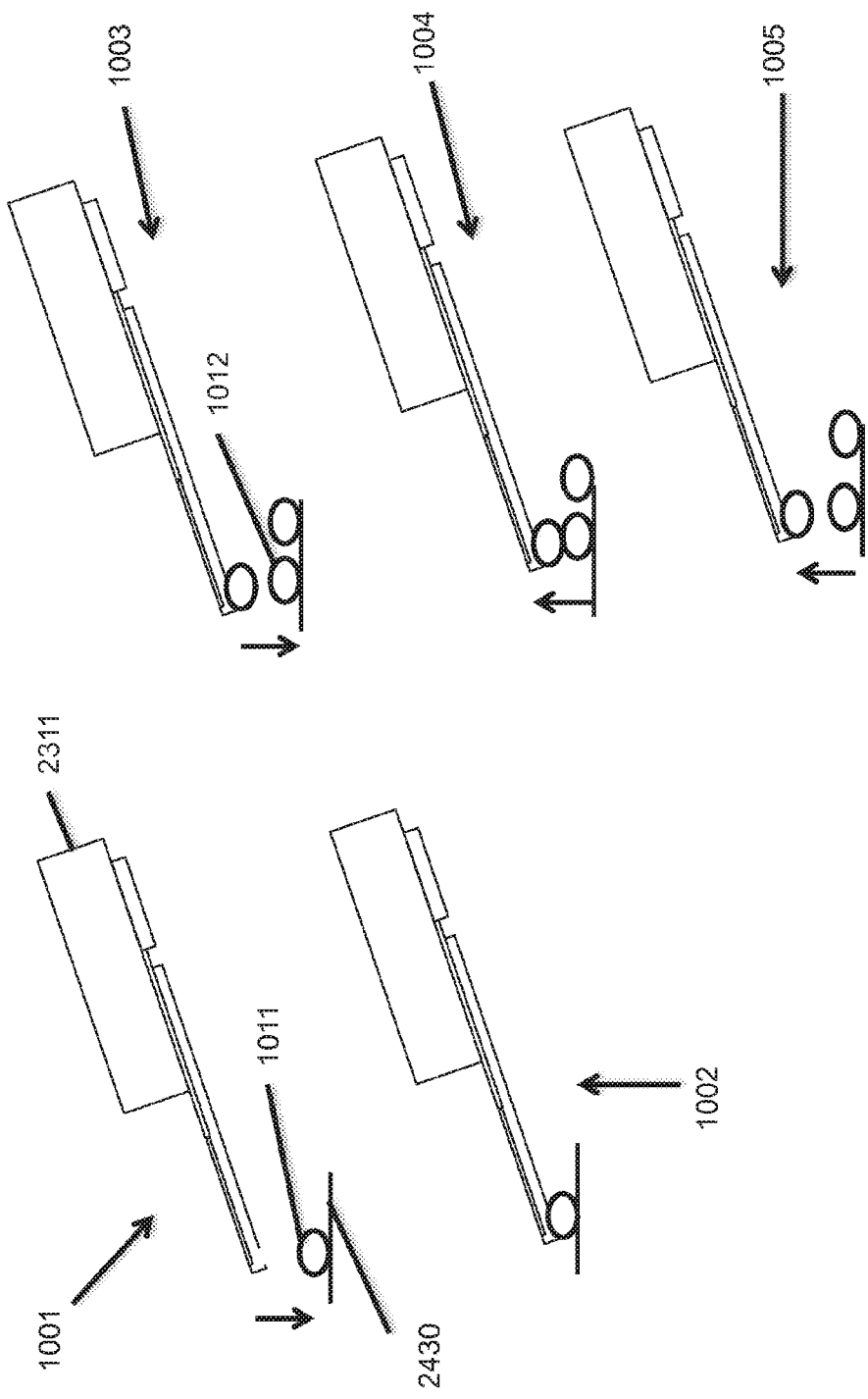

FIG. 10 shows various methods that the apparatus can used for. Suction is applied via a pump connected via a tube to the apparatus's main body (also referred to as substrate or chip). The tip is brought in contact with an item to be attached via suction (negative pressure) step 1001. The embedded sensors sense the contact. The arrows point to the direction of movement of the cantilever. In one embodiment a microscope (examples include optical, inverted, florescent, scanning electron microscope) is used to view the movement. Specialized micromanipulators (manual or motorized or piezoelectric or other or a combination of the aforementioned) are used to move the apparatus. The item is one of the following: a cell, a live cell, a bead (such as a functionalized micro-bead, antibody functionalized bead, a circulating tumor cell, a micro-particle, a nano-particle, or other item), any other particle of any shape. The item may be attached via suction on the outer part of the apparatus's distal end step 1002 or drawn inside the pipette's channel. Adhesion studies are enabled by bringing the dead or cell attached by suction to the opening of the cantilever step 1003 in contact with another cell or surface or particle step 1004(the cells adhere to the surface via antibody binding or other mechanism such as a net to hold the cell onto the surface) by monitoring the signal from the embedded displacement sensors. Then the apparatus is retracted and the strength of the binding is measured step 1005 using the sensors' sensing mechanism. In one embodiment biochemicals are added to enhance or retard adhesion in order to study various drug candidates. The hollow cantilever (pipette) has a protruding tip with an opening or it does not have a tip but it still has an opening. Other methods to attach a bead include gluing or burning the bead with a heater at the tip of a probe (for example using a cantilever with a nano-heater and heating the tip to melt the particle on the tip). In one embodiment the pipette draws a cell from a liquid media (optionally the cell is tagged with florescent die), thus the apparatus can selectively pick cells and deposit them in another location. If the cells are drawn inside the pipette then multiple cells can be drawn and removed from the liquid. Then the cells (or other items) can be transported to another location. This methods is then used for cell selection and sorting. For example cancer cells can be picked and moved to another location for analysis. The apparatus may include an analysis unit. Optionally the analysis unit includes one or more of the following: per, amplification, thermal cycling unit. In another embodiment building blocks are attached using step 1001 and step 1002, then are moved to another location, and then are deposited using positive pressure through the micro-channel pipette. This last process resembles building a structure using lego building blocks. This process is used to build structures. Additionally, the building blocks may be dipped in a glue to make the block stick to the rest of the structure. In one embodiment these methods are automated. For instance, the item is drawn by negative pressure onto the tip, the tip moves up and then to another location. The item is dipped in glue, then the cantilever is moved up again and to another location. Then positive pressure is applied to release the item at the desired location. The apparatus is operated in liquid or fluid or air or vacuum or partial vacuum or partial pressure.

Figure 11:
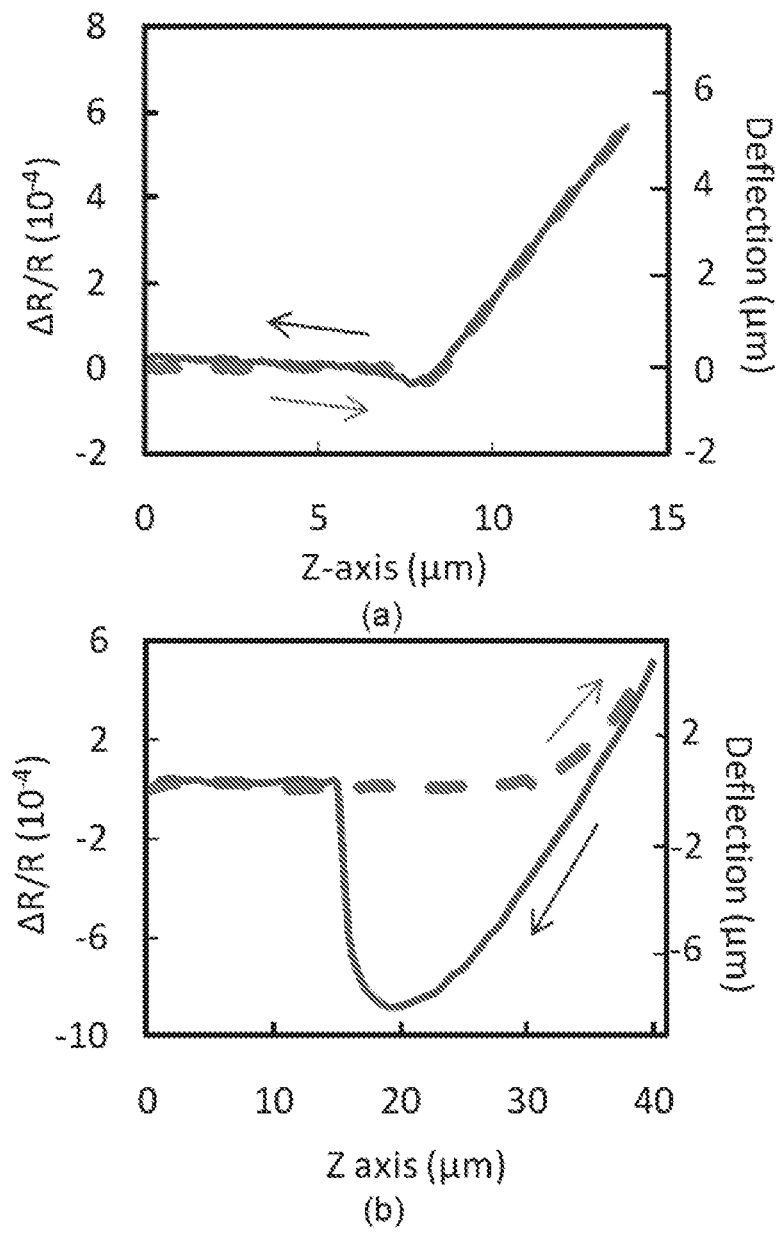
FIG. 11 show measured $\Delta R/R$ vs. out-of-plane probe movement (force-curve) on two different materials.

FIG. 11 show measured ΔR/R vs. out-of-plane probe movement (force-curve) on two different materials. Force-curves on: (a) a glass substrate; (b) another material are shown as examples. The arrows indicate the direction of the movement. The thick line represents the trace (probe and sample moving toward each other) and the thin line represents the re-trace (probe and sample moving away from each other). The vertical axes are ΔR/R on the left and corresponding calculated cantilever deflection on the right, and the horizontal axis is the Z-axis movement of the sensing element toward and away from the sample. Therefore the material of (b) has a stronger adhesion than (a). This technique is used to calibrate the sensing element. The output of the element is first measured on a hard surface and then it is calibrated. Then it is used to measure the adhesive forces as well as the softness of a sample (for example of a cell, polymer sample, cell culture).

Figure 12:
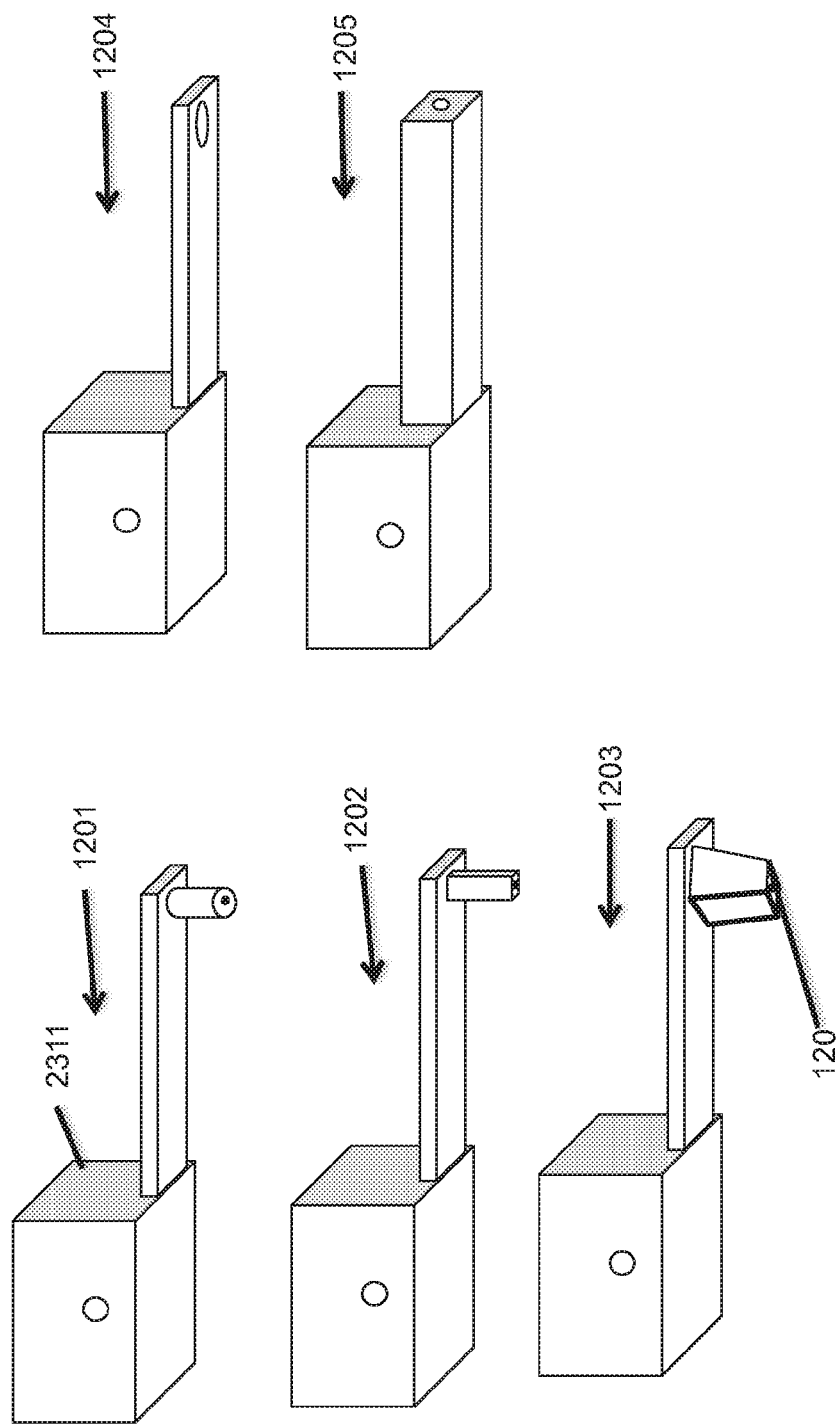
FIG. 12 illustrates various shapes of tips and openings including cylindrical (a), square (b), pyramid (c), tip-less openings (d) and (e).

FIG. 12 illustrates various shapes of tips and openings including cylindrical 1201, square 1202, pyramid 1203, tip-less openings 1204 and 1205. For example the tip 120 on the cantilever is a cylinder with an opening at the center of the cylinder and the micro-channel of the cantilever (micro-arm) connected to the opening in such a way that fluid (liquid or gas) can pass through the opening of the tip 120 and through the micro-channel in the cantilever to the chip fluidic unit and to a tube and a pump. In another embodiment fluid can flow from the tube to the fluidic channel and via the opening be deposited or applied onto an item near the tip 120.

Figure 13:
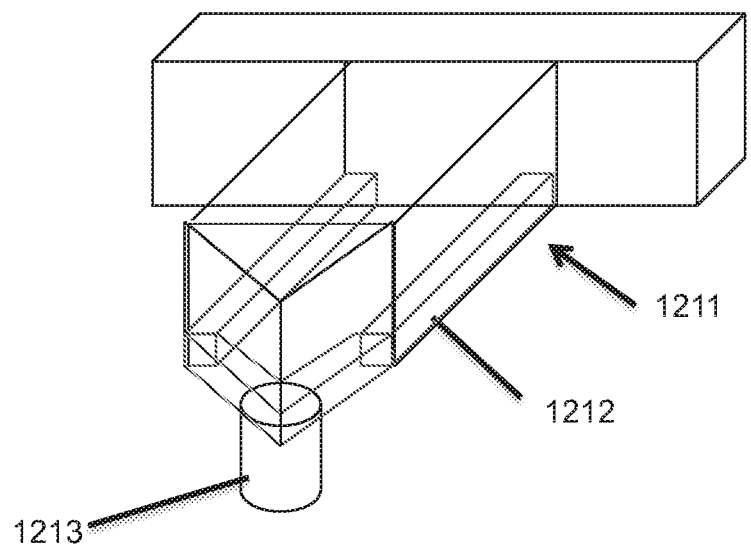
FIG. 13 illustrates a hollow microcantilever that in addition to the sensing elements (not shown) includes heater wires and a hollow tip.

FIG. 13 illustrates a hollow microcantilever 1211 that in addition to the sensing elements (not shown) includes heater wires 1212 and a hollow tip 1213.

Figures 14A, 14B, 14C:
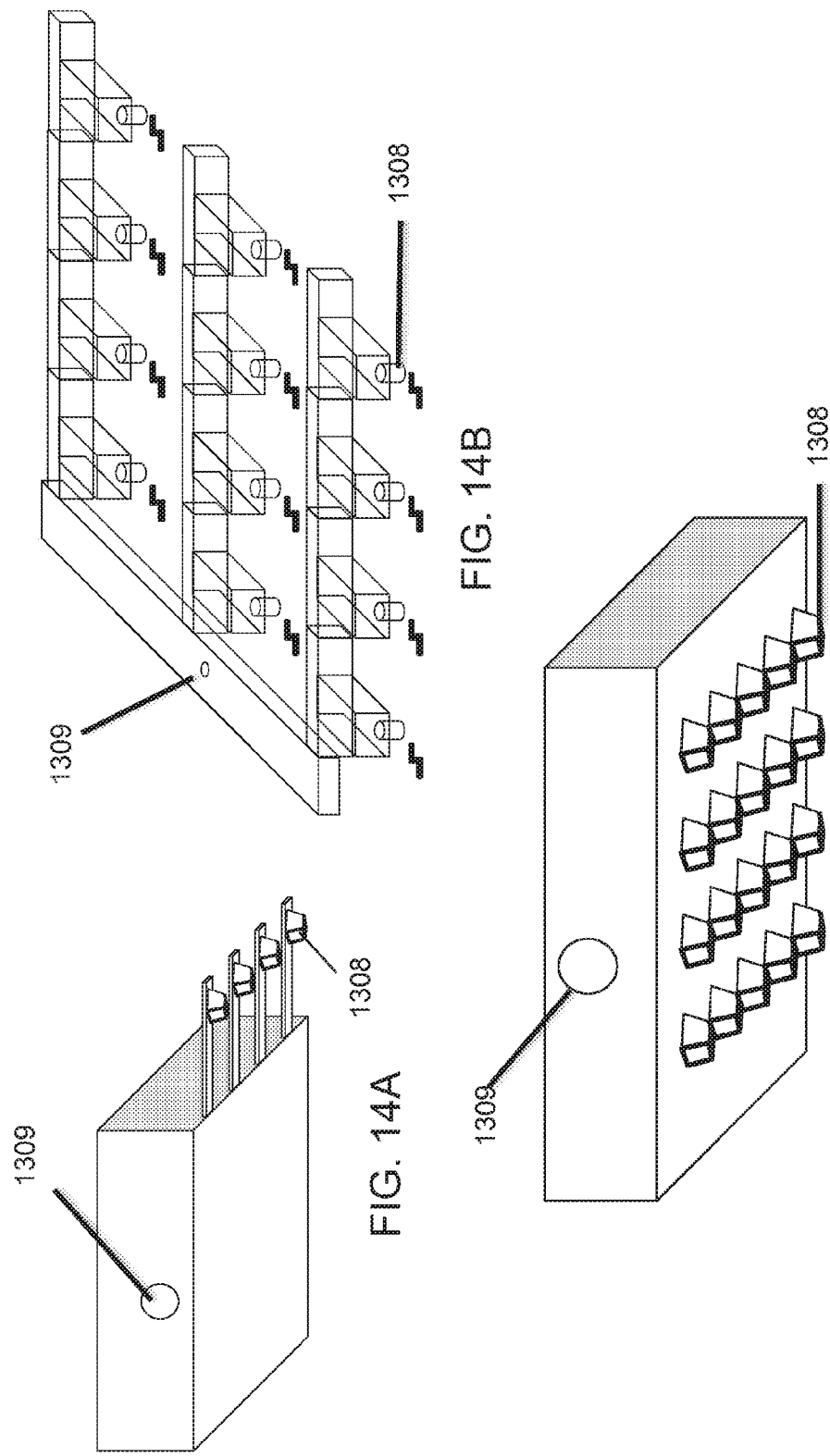
FIGS. 14A-14C show various arrays of cantilever probes with fluidic channels

FIGS. 14A-14C show various arrays of cantilever probes with fluidic channels (hollow cantilevers or pipettes or cantilever with micro-channel). The sensing mechanism is not shown in this figure. Openings 1309 are for pumping in or out the fluids (including liquid and gas). Openings 1309 can be placed on the side or the back of the chip (also referred to as substrate or main body) or the top or bottom. The cantilever and tip with an opening 1308 are shown in (b). FIG. 14A is a 1 dimensional array arrangement; FIG. 14B is 2 dimensional array of hollow cantilevers (suspended beams); FIG. 14C shows an apparatus with openings but without the cantilevers. In another embodiment the apparatus has multiple nanoscale openings and no elongated structure. The opening at the tip has a diameter between 1 nm and 60 micron. In certain embodiments of this invention each fluidic channel is independently connected to a tube and a pump, while in other embodiments there is one centralized tube and pump. Examples of uses include but are not limited to: (1) immobilizing cells on a glass cover slip and bringing the probe tips in contact with each cell for measurement or liquid delivery or both; (2) placing a sample such as a wafer on a hot-plate, heating the plate, bringing the probe tips in contact or in close proximity to the wafer, delivering gasses or liquids or mixtures of either or both, thereby creating a reaction such as a decomposition to occur.

FIGS. 15A-15C show the arrangement for patch-clamping and micro-injections. A cell 1404 rests on a glass slide with an inverted microscope (optionally equipped with florescence) under it (this slide may also rest on a piezoelectric stage or a motorized stage or both in order to be able to be moved in small distances), a micromanipulator 1405 with XYZ travel for probe movement (optionally a motorized stage is used and a piezo-electric stage) to control the movement of the probe (hollow cantilever) and bring it in close proximity to the cell 1404, the probe substrate and holder are equipped with a fluidic channel 1406 and connected to a fluid transport channel 1407 (connected to a fluidic delivery system and a pressure unit and a flow control unit and a fluid reservoir unit (not shown)), the cantilever 1412 (with the microchannel) on the chip (main body of apparatus) 1408 includes an electrode for patch clamping 1409 connected to patch clamp amplifier (not shown) and an embedded displacement sensor 1411, the cell and apparatus are immersed in buffer solution 1410. The sensor 1411 is used to track the probe's movement on the Z direction. The sensor and the piezoelectric stage are used to sense the force on the sample and measure elasticity as shown in FIG. 15A. When the tip contacts the sample the signal increases indicating that there is contact. This electrical feedback (either piezoelectric or piezoresistive) system on the cantilever can sense if the probe tip has broken into the membrane of the cell. It can also provide topographical information. Therefore, this tool combines scanning probe microscopy (SPM) probes with embedded sensing elements to sense movement and the patch-clamping technique to investigate the functions of single ion channels. The micromachined (MEMS) nanoscale patch clamp (nanopatch clamp) scanning probe and scanning system has the ability for agent delivery, imaging (morphology mapping with nanometer resolution), and electrophysiological measurements of cells as shown in FIG. 15B (typical patch clamping recording). The nanopatch clamp allows the visualization of subcellular structure. The same probe can function as a nanoscale syringe allowing stimulation of individual cells or parts of a cell through delivery of active agents from a solution. Injections may include proteins, drugs at the cell membrane or inside the cell to study the cells.

FIGS. 16A-16D illustrate fluidic delivery of a gas or a gas mixture or a liquid or a liquid mixture. A probe with a hollow tip (with an opening at the distal end) 1508 is brought in contact or close proximity with a substrate 1501. The entire system including the stages for moving the probe relative to the sample/substrate. The system is in room temperature and pressure or in a vacuum environment or inside a fluid. In one embodiment the substrate 1501 rests on a hot-plate to heat the substrate to sufficient temperature to induce a desired reaction. A fluid such as a precursor gas or a gas or a gas mixture or a liquid flows through the pipette to the tip and onto the substrate. As soon as the fluid contacts the substrate a reaction occurs. A gas is a hydrocarbon, an organometal, an organic material, or other material capable of growing on the substrate a grown material. Said grown material is selected from the group consisting of: dielectrics, titanium nitride, SiO2, silicon-germanium, silicon, silicon oxynitride, silicon nitride, silicon carbide, carbon nanotubes, carbon fiber, metals, and synthetic diamonds. A chamber may be included. Additional carrier or reaction gasses may be included in the chamber. A catalyst 1502 may be included. The grown structure 1503 is grown at the direction of motion of the tip relative to a first substrate 1507 and a second substrate 1505 (either one is moved relative to the other). An electrode may also be included 1534 to facilitate or induce the reaction with or without heating the substrate. This method can also be used for fluidic delivery or for inducing reactions such as a decomposition of a gas/gas mixture. The apparatus and substrate can be moved at a programmed rate to induce a reaction with on the substrate. A heater (resistor for example metal thin film) can be placed at the rim of the probe tip or near the tip's opening to heat the passing fluid (gas or liquid). The hollow tip and substrate operate in one of the following: air, or vacuum or partial vacuum or high pressure or low pressure or liquid.

Figure 17:
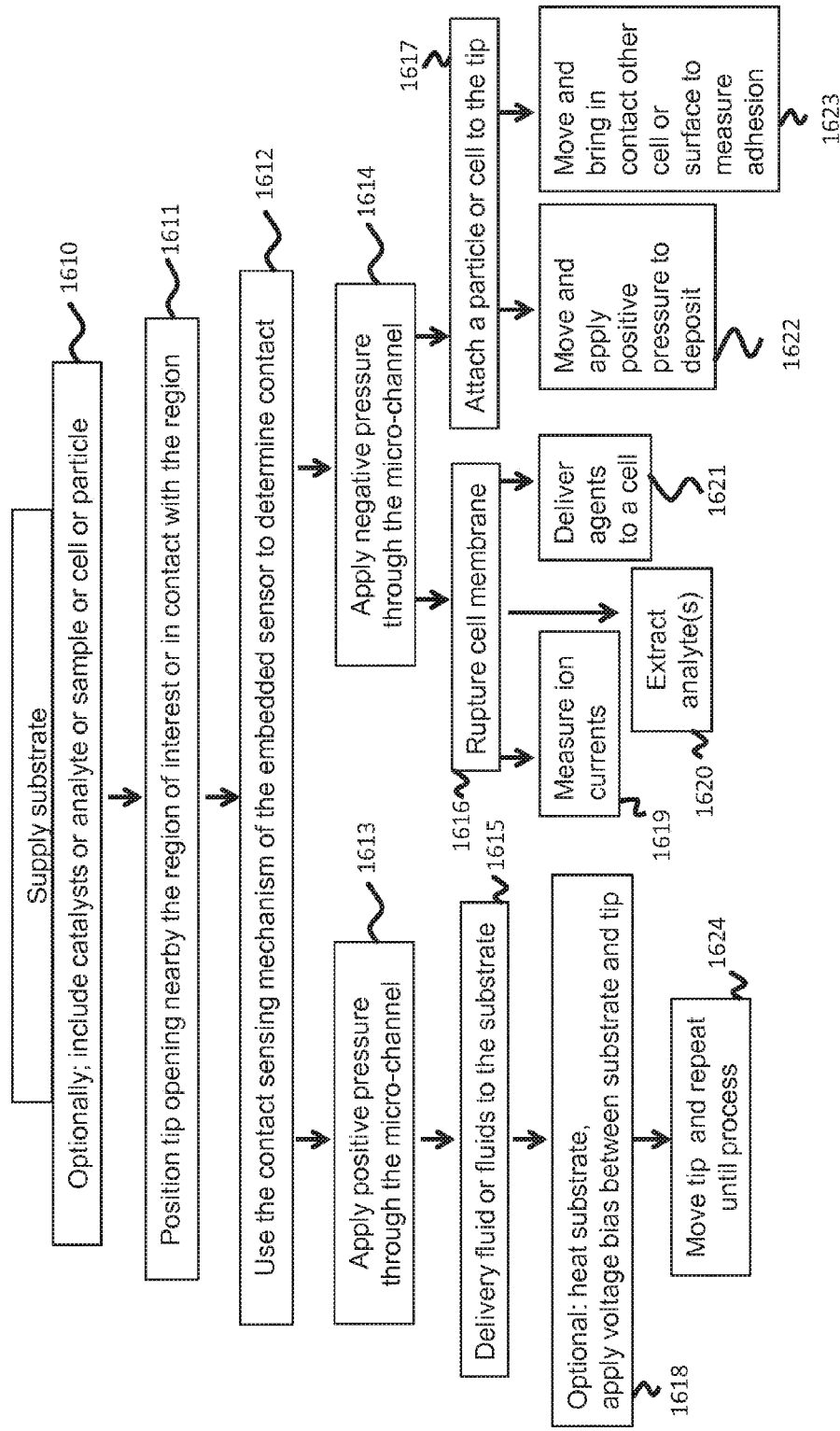
FIG. 17 shows the various process flows and methods for using the apparatus.

FIG. 17 shows the various process flows and methods for using the apparatus as described above.

Figure 18:
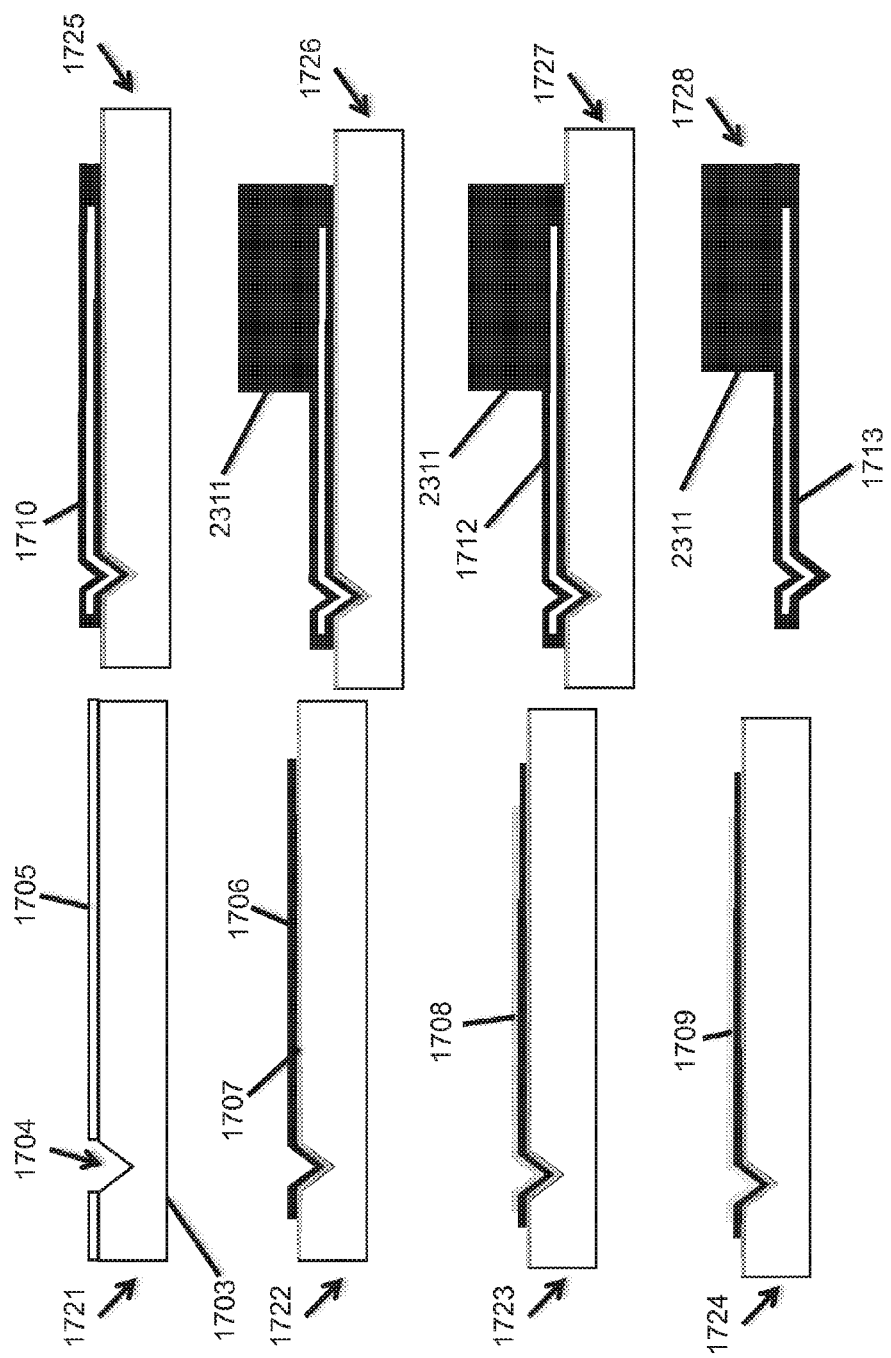
FIG. 18 illustrates a fabrication process for the apparatus.

FIG. 18 illustrates a fabrication process for the apparatus. There are several other ways to fabricate similar devices. The fabrication requires the following steps: step 1721 A silicon substrate 1703 with silicon oxide 1705 is etched to form a notch. Silicon oxidation can be used for sharpening 1704. step 1722 Titanium 1707 is used as a sacrificial layer and polymer is deposited 1706. step 1723 an additional sacrificial layer is added 1708, step 1724 electrodes for patch clamping as well and the sensors for sensing deflection 1709, step 1725 the second polymer layer is deposited 1710, step 1726 a substrate (main body) is deposited from SU-8 1711, step 1727 the sacrificial layer is removed 1712, step 1728 FIB to make hole metal backside deposition for reflectance 1713. Planarization can also be used to make a hole.

Figure 19:
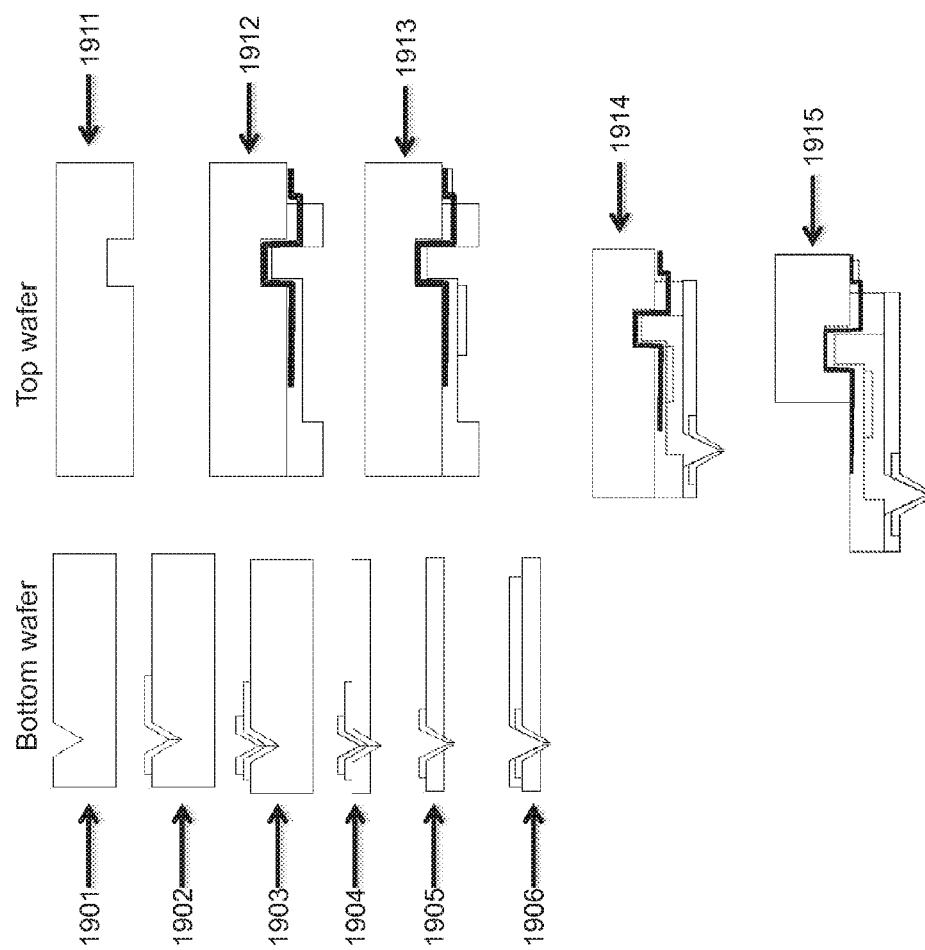
FIG. 19 shows another fabrication process for polymers or elastomers or silicon-nitride or other materials that can be deposited.

FIG. 19 shows another fabrication process for polymers or elastomers or silicon-nitride or other materials that can be deposited. This process relies on wafer bonding. The bottom wafer step 1901 is first anisotropic ally etched to for a notch. Then oxide is grown step 1902. Then chrome is deposited step 1903 and it is etched with BHF step 1904. Following that the oxide and chrome are removed step 1905. The polymer is deposited (or any material that is to form the cantilever) step 1906. The top silicon wafer now is first dry reactive ion etching (DRIE) etched and oxidized the top step 1911. Then the material for the cantilever is deposited and the sensing material is also deposited step 1912. The metal electrode is deposited at this time step 1913. The top and bottom wafers are bonded by thermal compression bonding step 1914. Finally XeF2 is used to remove silicon from the cantilever area while masking the rest of the apparatus step 1915.

Figure 20:
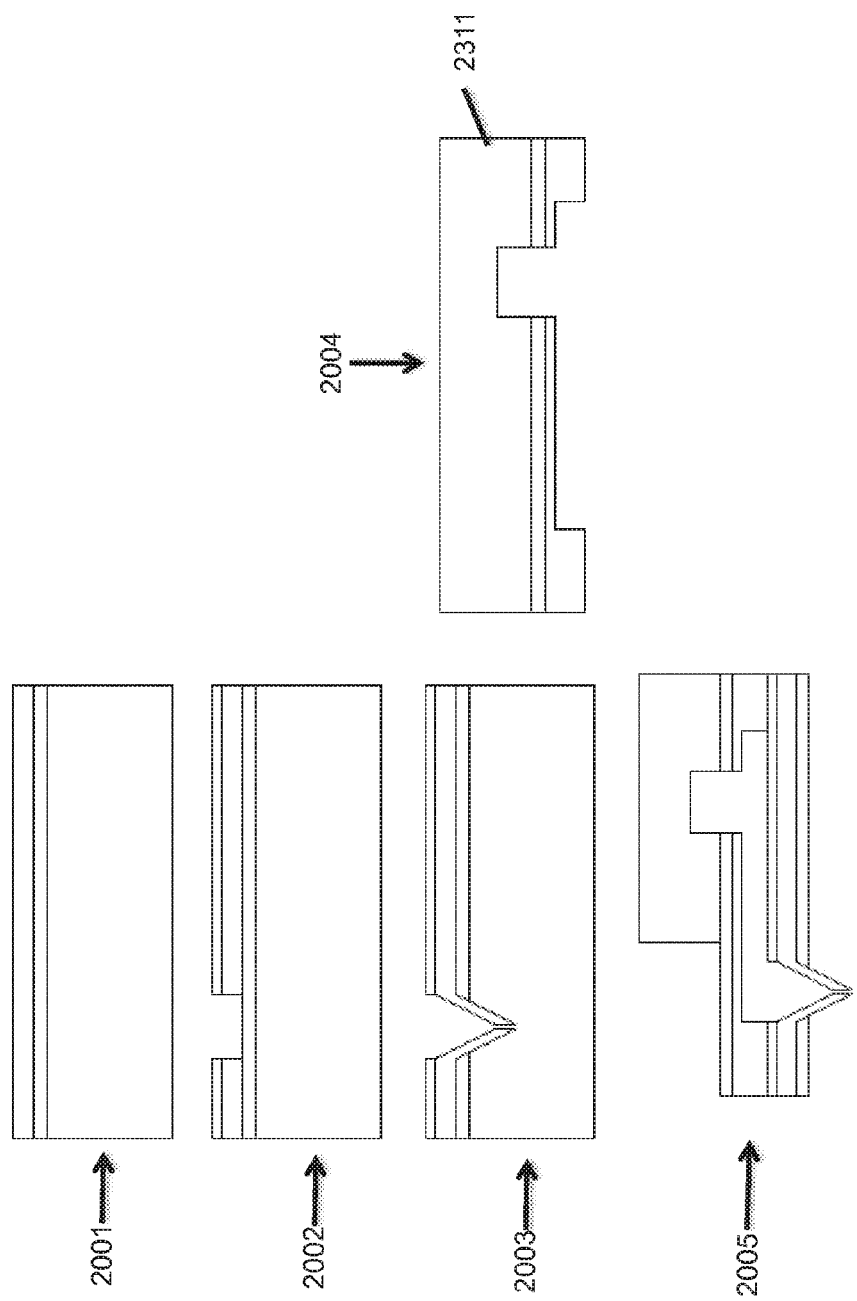
FIG. 20 shows a fabrication process that starts with an SOI wafer.

FIG. 20 shows a fabrication process that starts with an SOI wafer. This process relies on wafer bonding. The bottom wafer step 2001 is first etched after oxide is deposited on the top silicon step 2002. Then it is anisotropic etched to form a notch, chrome is deposited, and it is etched with BHF step 2003. Following that the oxide and chrome are removed. The top silicon wafer is first DRIE etched and oxidized to form a micro-fluidic channel. The metal electrode and sensing elements are deposited at this time. The top and bottom wafers are bonded step 2004. Finally XeF2 is used to remove silicon from the cantilever area while masking the rest of the apparatus step 2005.

In one embodiment the lab-on-a-pipette' apparatus integrates a micro-aspiration tip (also referred as hollow tip, hollow cantilever, micro-syringe) with microfluidic analysis components (or micro-fluidic module or fluidic unit) to conduct in-situ, real-time single cell genetic diagnosis in a single disposable apparatus. The micro-aspiration tip extracts and encapsulates a cell into an ultra-low volume plug (~300 pL). The fluidic module includes optical analysis chambers.

One skilled in the art may fabricate similar apparatus (devices) from SU-8, polymer, silicon, silicon nitride, glass, silicon carbide or other materials or a combination of these materials using micro-fabrication (MEMS technology) or other techniques. The electrode material could be made of any metal including silver-chloride, gold, platinum, chrome, silver. The apparatus including the pipette (hollow cantilever or hollow tip) are monitored by a variety of methods including: an upright or inverted microscope, scanning electron microscope. There are several methods of fixing a cell on a substrate including the use of antibodies on specific locations on a substrate so that the cells attach to those locations, applying suction from under the substrate via predefined holes to draw cells to the predefined locations. In a specific embodiment a planar patch clamp is used to fix cells and the elongated hollow structure is brought in contact with the cell fixed by the pressure applied to measure the ion current or extract or deliver an item. In a specific embodiment a planar patch clamp is used to fix cells and the elongated hollow structure carrying a cell or some other item is brought in contact with the cell fixed by the pressure applied of the planar patch clamp, then a number of processes such as adhesion measurements are completed. A micromanipulator is used to control the apparatus (probe) or the substrate or both relative to each other. A micromanipulator is one of or a combination of: a piezoelectric stage, a motorized stage, a magnetic stage, a manually controlled stage. Cells may be picked up via a pipette or magnetic means. For example attach magnetic particles functionalized with antibodies to stick only to cells of interest and using a magnetic micro-pick pen (or wire or probe) to pick and drop cells to a location for measurement. The micro-fluidic chip can be integrated with other devices that interact with environment with various electronics and hardware. The apparatus described can also be retrofitted to operate like a neural probe. One skilled in the art may use similar fabrication processes described or devices similar to the ones described to fabricate neural probes from polymer (such as parylene, SU-8, polyimide, PDMS, elastomers). Furthermore, neural probes fabricated directly on a PCB eliminate steps such as wire-bonding and gluing. The apparatus described may also be used as an optical probe to record light of specific wavelength for example this apparatus can be used to detect optically stimulated neurons that are excited or inhibited by light. Similarly, a thermal probe or micro-heater can be directly fabricated on a PCB. A wafer size PCB with predefined wires, vias, connector, pads, may already have the substrate of main body of apparatus patterned and connected with other parts with small-arms. The fluidic section and cantilever can be directly deposited onto the PCB. A flexible PCB can also be used.

Conductive polymers can also be used (instead of metals, metal oxides, or doped silicon) for sensing displacement, movement, thermal, as well as for heating. For example conductive piezo-resistive polymers and piezoresistive polymer composites (such as Panipol) can be used to sense bending or other properties or movement. Likewise intrinsically conducting polymers (ICPs) that are organic polymers that conduct electricity can be used. One skilled in the art can fabricate a cantilever made entirely of piezoresistive polymer composites to detect stress, bending, pressure changes, and other changes.

A cantilever such as a hollow cantilever fabricated on and integrated with a printed circuit board (PCB) eliminates several issues with packaging such as wire-bonding and connecting the apparatus to external electrical power and measurement devices. This concept relates to MEMS on PCB where entire systems are directly fabricated on a PCB instead of silicon wafer. The benefit of using PCBs is that the PCB can have pre-fabricated vias, interconnects, pads, and wires thus the devices can be fabricated directly making contact with these PCB wires and pads simplifying the packaging and avoiding cumbersome and expensive wire-bonding.

The cantilever may have more than one fluidic channels. For instance it may have two channels that are connected at the tip. As mentioned above, polymer (such as SU-8) may be used with an embedded piezoresistor without a sharp tip. Therefore the opening at the distal end of the cantilever may be flat. The cantilever varies in dimensions for example it may be 20 micron×80 micron with a thickness of 1-2 micron. Soft cantilevers made from a polymer are ideal for elastography and adhesion measurements of cells in liquid media.

The item is selected from the group consisting essentially of a cell, a live cell, a bead, a functionalized micro-bead dispersed on cells in a cell culture, extracellular matrix, antibody functionalized bead, a protein coated particle, a circulating tumor cell, a micro-particle, a nano-particle, an item, any particle of any shape, a sphere, a cube, a block, a substrate, a surface, a device, or the like.

FIGS. 21A-21C illustrate an application of the hollow cantilever probe. This application is an extension of FIG. 11.

Figure 22:
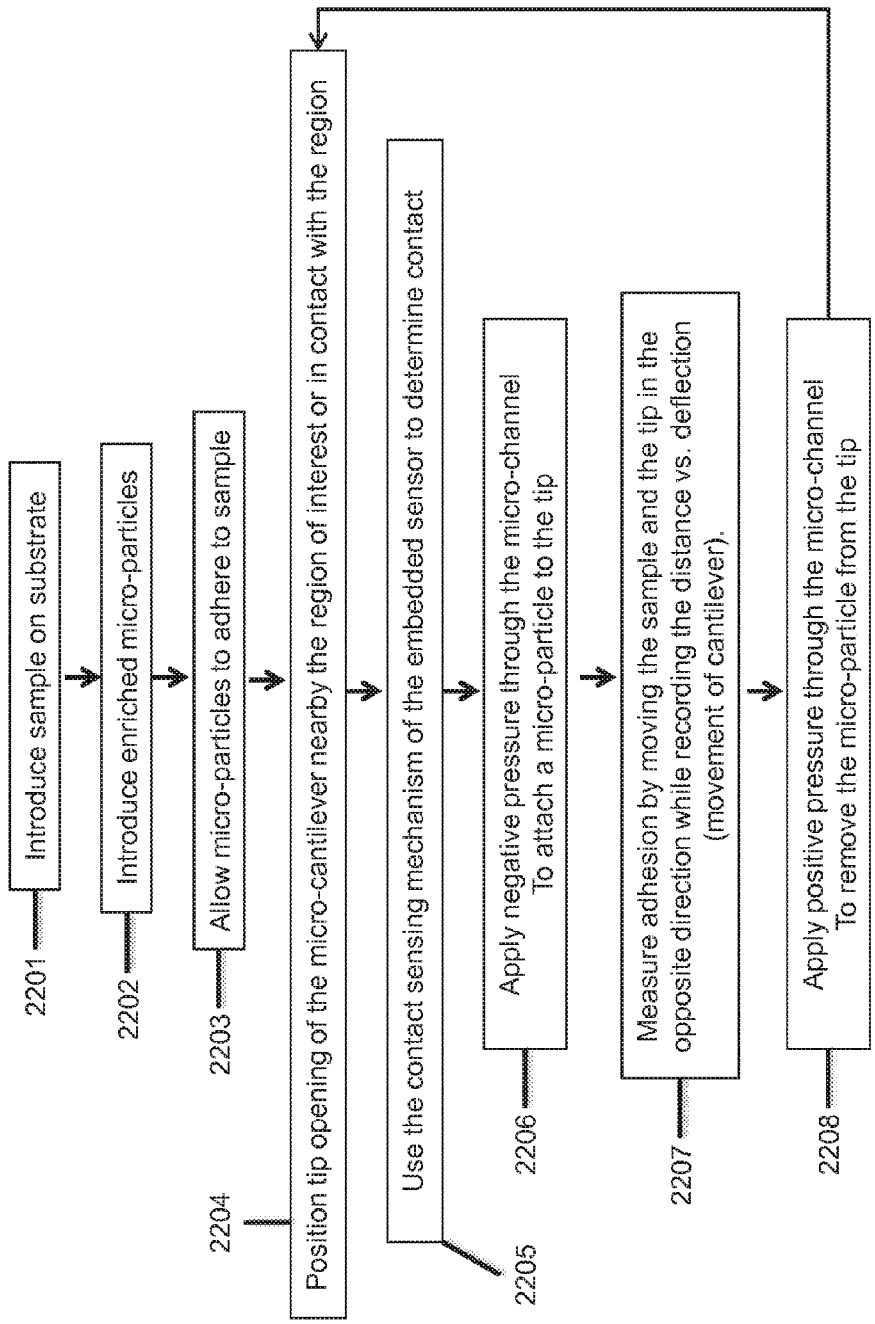
FIG. 22 shows the process flow and method for using the apparatus of FIG. 21.

The application and method relates to high throughput adhesion measurements of a sample for instance a material or cell membrane proteins, peptides, other bio-molecules or other materials. Samples (live cells or any material to be tested for adhesion) 2118 are fixed or cultured or grown) or in media on a substrate 2119. Examples of substrates are a cover-slip or Petri dish or Petri plate or cell culture dish or a slide. Functionalize beads such as micro- or nano-particles (also known as microbeads, micro-particles, microspheres) are introduced. These micron size particles 2101 have attached on part of their exterior at least one type of a material 2102, such as ligand or antibody or peptide or other bio-molecule or other molecule, that will bind to a cell 2118 or the material under test (are enriched with or functionalized). Micro-size particles may have coating on their exterior 2103. Microspheres or similar micro-particles are routinely used in cell diagnostics and biological applications. In one embodiment of this application the micro-particles may have different binding materials 2102 (such as ligand or antibody or peptide or other bio-molecule or other molecule) that will bind to the material under test. For example: micro-particles A have antibody A, micro-particles B have antibody B, micro-particles C have antibody C. Micro-particles A, B, and C are all introduced on the sample and left for enough time (from a few seconds to several hours) to bind to the sample (such as material or cell). A hollow cantilever apparatus 2141 like the ones described in this disclosure with an opening at its distal end (the opening at the tip or along the cantilever without a tip and the tip being of any shape) with a sensing mechanism (sensing mechanisms include embedded sensing mechanisms such as piezoelectric or piezoresistive or other type or laser optical lever such as the one used in atomic force microscopes also known as force-feedback mechanism) brought in contact with a micro-particle. Then suction is applied (negative pressure) via means to generate fluidic flow are used (with bi-directional capabilities able to create a pressure, a vaccum, positive and negative pressures) such as a micro-pump or other pumping mechanism for the micro-particle to be partially drawn to the opening by establishing a partial vacuum (much like a holding pipette). Then as shown in FIG. 21C, the hollow cantilever is moved upwards puling the micro-particle away from the sample, while the "force vs. distance" curve of movement is recorded as shown in FIG. 21B. For example if a piezo-resistive sensing element is used then the distance of movement of the substrate in relation to the hollow cantilever vs. the change in resistance of the piezo-resistive element is recorded. This can then be converted to distance or force or normalized. Likewise the same measurement can be done with an optical lever or some other mechanism. This way the strength of the binding between the particle and the sample can be measured. The hollow micro-cantilever apparatus 2141 is then moved to a different location over another micro-particle and the process is repeated. The second micro-particle may be coated with another material such as another antibody of a different kind, that way when the process is repeated the binding strength and the binding of the other antibody with the material under test (such as a cell) can also be tested. The process is repeated a number of times. The micro-particles may have florescent die or other color based tagging so that they can be differentiated when contacted, measured, and tested. This technique allows for multiple adhesion studies of different materials to be tested very quickly on the same sample. For instance, the user monitoring through a microscope (eg. inverted florescent microscope) indentifies microsphere 2101 A (by its color or florescent signature). Then the user guides the hollow probe 2141 over sphere A, brings the hollow tip 2141 in contact with the sphere 2101 while monitoring the signal of the embedded sensor to determine contact (a signal such as the one in the inset graph for moving toward the sample is produced). Then suction is applied to attach the micro-sphere to the tip of the probe. As soon as good attachment is established the cantilever and the sample are moved in the opposite direction while the signal is monitored (a signal such as the one in the inset graph for moving away from the sample is produced). This signal provides the user with information about the existence of adhesion and the strength of adhesion. If adhesion is not very strong then the sphere will detach from the sample and will remain on the tip. The tip then is moved to another location and positive pressure is applied to remove the sphere from the tip. Then the cantilever is moved to sphere B, which may have different antibodies attached to it, in order to measure their adhesion and the entire process is repeated again. FIG. 22 shows the process flow and method for using the apparatus of FIG. 21.

In another embodiment a polymeric robotic micro-arm with opening and embedded sensing mechanism has a hollow inner tube and an opening at its distal end. The device includes a sensing mechanism to detect contact and the degree of contact or pressure exerted on the contacted area. In one embodiment the sensing mechanism detects only contact in the Z-axis (up-down) and in another an additional sensing mechanism detects Y-axis (left-right) contact and degree of contact pressure. For example in FIG. 7 there are two sensors 118 and 120. The sensing element or sensor 120 senses up-down movement (vertical) and the sensor 118 senses left-right (horizontal). In one embodiment additional sensing mechanisms such as temperature sensing and an electrode for current and voltage sensing are also included. In one embodiment the arm includes a heater near the opening, at the opening, or inside the arm. The entire arm is fabricated from a polymer material. Polymeric materials include but are not limited to: SU-8, elastomer, polyimide, silicone, PDMS, and parylene. The sensing mechanism is a piezoresistive, or a piezoelectric, or elastoresistive or conductive polymer or metal thin film or doped silicon or a metal oxide or elasto-resistive or of other type. In addition, in one embodiment the substrate includes fluidic tubes. Several fabrication methodologies are described. The apparatus includes a sensing mechanism to detect contact and the degree of contact or pressure exerted on the contacted area (elements 118 and/or 120 in FIG. 7). In one embodiment the resistance change or some other electrical change (such as current or voltage) of the sensing mechanism is monitored with an external electrical measurement device (such as a multi-meter, voltmeter, source meter, resistance meter). External wires connect the apparatus to the external electrical measurement device. In one embodiment the sensing mechanism is a thin film of metal or metal oxide such as gold. The arm rests on a substrate. The substrate is one of the following: silicon, silicon with a thin layer of oxide, or silicon nitride, or glass, or SU-8, or part of a printed circuit board (PCB), or a polymer, or a combination of the aforementioned. In one embodiment the substrate includes electrical pads. In addition, in one embodiment the substrate includes fluidic tubes. Several fabrication methodologies are described. In the preferred embodiment a polymeric robotic micro-arm with opening and embedded sensing mechanism posses a hollow inner tube and an opening at its distal end. The apparatus includes a sensing mechanism to detect contact and the degree of contact or pressure exerted on the contacted area. In one embodiment the substrate includes electrical pads. In addition, in one embodiment the substrate includes fluidic tubes. In one embodiment tubes are flexible tubes.

In one embodiment, in fabricating polymer cantilevers with embedded deflection sensing elements the sensing element is a thin film of Cr/Au with 2 nm/10 nm thickness. The first polymer layer is 1.5 micron thick. The sensing element deposited. Then 0.5 micron of polymer is deposited to form the top layer. A $3 \times 1.4 \times 0.5$ mm$^3$ chip serves as the base of the cantilever (main body). The polymer cantilevers is wired to establish electrical contact and then insulated with PDMS to insulate the electrical contacts. In the preferred embodiment the sensing element is sandwiched (or otherwise deposited between or embedded between) two layers of polymer.

Figure 23:
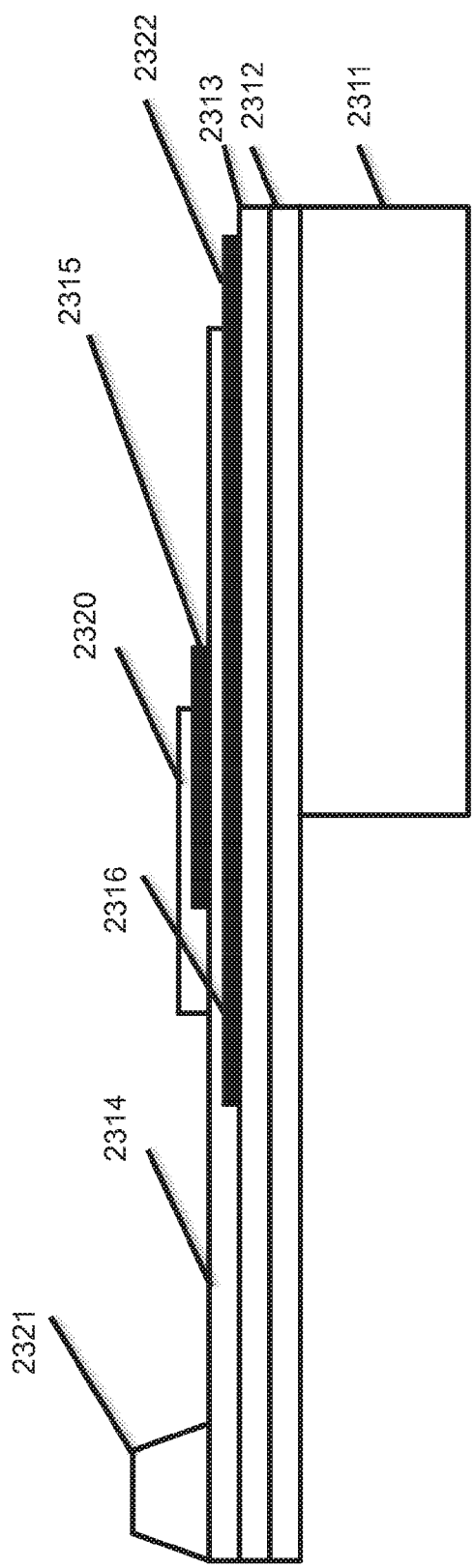
FIG. 23 shows an embodiment with three polymer layers.

In the preferred embodiment one of the two layers of polymer being thicker than the other layer of polymer. In one embodiment a third layer is included. FIG. 23 shows an embodiment with three polymer layers. For example, on the main body 2311, (a) a first layer of polymer is deposited and forms the bottom part of the apparatus 2312, (b) then a second layer forms the walls of the fluidic channel (hollow structure) 2313, (c) then a third layer covers the top to complete the formation of the hollow structure (this layer also includes the opening at the distal end) 2314, (d) then the sensing element is deposited, and 2315 (e) finally an additional layer is deposited to insulate the sensing element 2320 (this layer is thinner than the 2311 and 2312). In one embodiment the final layer 2320 is thinner than the rest of the layers. A tip with an opening is also included 2321. In another embodiment (a) a first layer of polymer is deposited and forms the outer wall of the apparatus, (b) the electrode is deposited 2322, (c) then a second layer forms the walls of the fluidic channel (hollow structure), (d) then a third layer covers the top to complete the formation of the hollow structure, (e) then the sensing element is deposited, and (f) finally an additional layer is deposited to insulate the sensing element.

Figure 24:
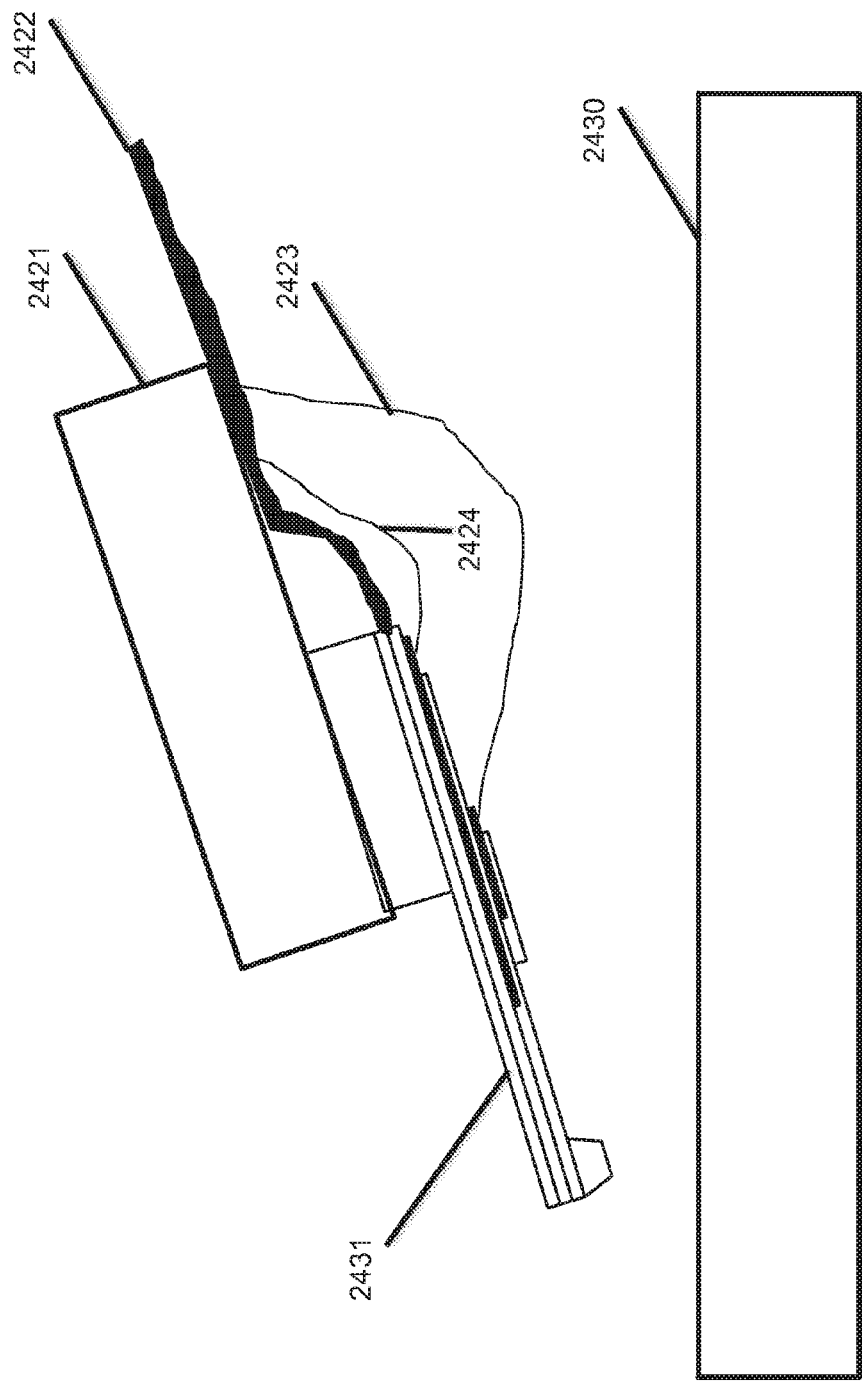
In FIG. 24, the device of FIG. 23 is attached on a holder.

In FIG. 24, the device of FIG. 23 is attached on a holder 2421. A flexible tube 2422 from the fluidic channel (hollow structure) connects the opening to a pump, a flow meter, and a flow control valve to provide pressure, to control and measure the flow of a fluid through the hollow structure at the opening (these are used as means to generate fluidic flow with bi-directional capabilities able to create a pressure, a vacuum, positive and negative pressures). Wiring 2424 connecting the electrode to a voltage source is shown. Wiring 2423 connecting the sensing element to a voltmeter or an ohm-meter or a current meter are also included. The holder is attached to a micro-manipulator (not shown) to move the device near the substrate. The sensing element 2315, the electrode, and the wiring 2423 and 2424 are insulated with a polymer (for example parylene or PDMS or an elastomer). The substrate 2430 rests (or part of it rests) on a stage selected from the group consisting essentially of a piezo-electric stage, a motorized stage, and a manual stage, or the like. One or more stages are used. The substrate is selected from the group consisting essentially of a glass slide, a wafer, a flat piece of material. A microscope either over the substrate or underneath it is used to monitor movement.

In one embodiment, a method to use a polymeric micro-arm apparatus is disclosed. The method comprising: a substrate 2430; an apparatus (FIG. 24), wherein the apparatus comprising: an elongated hollow polymeric structure with a distal end and a proximal end 2431; an opening near the distal end (117, 804); means to move the polymeric apparatus and the substrate in relation to each other (for example a piezo-electric stage, a motorized stage, or the like); means to monitor and measure the movement of the polymeric apparatus and the substrate in relation to each other (for example an optical microscope, a scanning electron microscope, a stage, or the like); the polymeric structure attached to a main body 2311; a pump, a flow meter, and a flow control valve to provide pressure, to control and measure the flow of a fluid through the hollow structure at the opening (used as means to generate fluidic flow with bi-directional capabilities able to create a pressure, a vacuum, positive and negative pressures); an element embedded in the structure configured to output a signal indicative and a measure of the bending of the structure (2315, 1411, 909, 118,120, 805); placing an item (1404,1502, 1501, 2118, 1011) in proximity or on the substrate; bringing the item and the apparatus in close proximity to each other; monitoring the signal of the element to determine contact between the apparatus and an item (FIG. 11, FIG. 15 (*a*)); contacting the item; wherein the item (1404,1502, 1501, 2118, 1011) is selected from the group consisting essentially of a cell, a sample, and a surface or the like. To further specify the embodiment the polymeric structure material of construction is selected from the group consisting essentially of a polymer, an elastomer, SU-8, polyimide, silicone, PDMS, and parylene, or the like. To further specify the embodiment the element is a resistor with a material of construction selected from the group consisting essentially of conductive polymer and metal thin film, or the like. To further specify the embodiment the element is a resistor configured to output an electrical signal indicative of the change of the electrical resistance indicative, the change of the electrical resistance being a measure of the bending of the structure (FIG. 11, FIG. 15 (*a*)). To further specify the embodiment the apparatus further comprises an electrode functionally attached inside the polymeric structure (1409) and another electrode in contact or in proximity (1451) with the substrate. To further specify the embodiment the apparatus delivers a fluid on the item (FIG. 16, FIG. 15). To further specify the embodiment the fluid reacts on the item to produce a solid material (FIG. 16). To further specify the embodiment the substrate is heated. To further specify the embodiment the structure is in contact with a cell membrane to study of ionic current, membrane potential, ion channels on the cell (FIG. 15). To further specify the embodiment the apparatus further comprises a resistor functionally attached inside the polymeric structure. To further specify the embodiment the resistor is configured to provide heating or to measure temperature. To further specify the embodiment the means to move the polymeric structure is configured to provide movement along both the z-axis and y-axis. To further specify the embodiment the means to measure the polymeric structure movement is configured to provide measurement along both the z-axis and y-axis.

In another embodiment a method to use a polymeric micro-arm apparatus is disclosed, the method comprising: a substrate; an apparatus, wherein the apparatus comprising: an elongated hollow polymeric structure with a distal end and a proximal end; an opening near the distal end; means to move the polymeric apparatus and the substrate in relation to each other; means to monitor and measure the movement of the polymeric apparatus and the substrate in relation to each other; the polymeric structure attached to a main body; a pump, a flow meter, and a flow control valve to provide pressure, to control and measure the flow of a fluid through the hollow structure at the opening; an element embedded in the structure configured to output a signal indicative and a measure of the bending of the structure; placing a first item and a second item in proximity or on the substrate; bringing the first item and the apparatus in close proximity to each other (FIGS. 10 (*a*) and (*b*)); monitoring the signal (FIG. 11) of the element to determine contact between the apparatus and a first item (FIG. 10 (*b*)); contacting the first item; wherein the first item is selected from the group consisting essentially of a cell, a live cell, a bead, a functionalized micro-bead, antibody functionalized bead, a circulating tumor cell, a suspended cell, a micro-particle, a nano-particle, an item, any particle of any shape, a sphere, a cube, a block, or the like (1404,1502, 1501, 2118, 1011); applying pressure in order to attach the first item onto the opening (FIGS. 10 (*b*) and (*c*)); moving the apparatus to another location; bringing the second item and the apparatus in close proximity to each other (FIG. 10 (*c*)); monitoring the signal of the element to determine the contact (FIG. 11) between the first item and a second item resting 1012 on the substrate (FIG. 10 (*d*)); contacting the second item (FIG. 10 (*d*)); the second item 1012 is selected from the group consisting essentially of a cell, a live cell, a bead, a functionalized micro-bead, antibody functionalized bead, a circulating tumor cell, a micro-particle, a nano-particle, an item, a particle, a sphere, a cube, a block, a substrate, a surface, or the like. To further specify the embodiment first item adheres to second item and wherein the apparatus and the substrate are moved away from each other and the strength of adhesion between the first item and the second item is measured using the element (FIG. 11). To further specify the embodiment first item is drawn in the polymeric structure (FIG. 1 (*a*)). To further specify the embodiment positive pressure is applied to remove the first item and deposit it on the second item. To further specify the embodiment first item has a distinct color or florescence in order to be identifiable. To further specify the embodiment the process is repeated in order to construct a structure.

To further specify the embodiment the an element embedded in the polymeric structure is configured to detect when the polymeric structure contacts an object resting on a surface and measures the force that the object exerts upon the polymeric structure.

In yet another embodiment a method to use a polymeric micro-arm apparatus is disclosed, the method comprising: a substrate; an apparatus, wherein the apparatus comprising: an elongated hollow polymeric structure with a distal end and a proximal end; an opening near the distal end; means to move the polymeric apparatus and the substrate in relation to each other; means to monitor and measure the movement of the polymeric apparatus and the substrate in relation to each other; the polymeric structure attached to a main body; a pump, a flow meter, and a flow control valve to provide pressure, to control and measure the flow of a fluid through the hollow structure at the opening; an element embedded in the structure configured to output a signal indicative and a measure of the bending of the structure; positioning an item on the substrate; dispersing particles coated with material on an item 2118; the item is selected from the group consisting essentially of a cell, a live cell, a cell culture, extracellular matrix, a particle, a sphere, a cube, a block, a substrate, a surface, a device; the particles 2101 are selected from the group consisting essentially of a bead, microbead, antibody functionalized bead, a protein coated particle, a micro-particle, a nano-particle, a particle, a sphere, a cube, a block, a device, a microsphere, or the like; the material 2102 is selected from the group consisting essentially of antibodies, proteins, bacteria, coatings, bio-molecules, molecules, organic molecules, inorganic molecules, polymers, or the like; bringing the item and the apparatus in close proximity to each other; monitoring the signal of the element to determine the contact between the apparatus and the particle (FIG. 21); contacting the particle (FIG. 21 (*b*)); applying pressure to attach the particle on the opening; moving the apparatus and the item in opposite direction from each other (FIG. 21 (*b*)); measuring the output signal of the element (FIG. 21), the signal being indicative of the adhesive force between the item and the particle. To further specify the embodiment groups of particles with different coatings each group identifiable by color or florescent coding are distributed on item. To further specify the embodiment positive pressure is applied to remove the tip from the particle and the process is repeated in order to measure the adhesion between the item and another particle.

In another embodiment a method to use a polymeric micro-arm apparatus is claimed, the method comprising: a substrate (also referred to as surface) 2119; an apparatus 2141, wherein the apparatus comprising: an elongated hollow polymeric structure with a distal end and a proximal end; an opening near the distal end; means to move the polymeric apparatus and the substrate in relation to each other; means to monitor and measure the movement of the polymeric apparatus and the substrate in relation to each other; the polymeric structure attached to a main body 2311; a pump, a flow meter, and a flow control valve to provide pressure, to control and measure the flow of a fluid through the hollow structure at the opening; an element embedded in the structure configured to output a signal indicative and a measure of the bending of the structure; positioning an item 2118 on the substrate 2119; dispersing particles 2103; bringing one of the particles and the apparatus in close proximity to each other (FIG. 21); monitoring the signal of the element to determine the contact between the apparatus and the particle; contacting the particle (FIG. 21 (*b*)); applying pressure to attach the particle on the opening; moving the apparatus and the item in opposite direction from each other; measuring the output signal of the element, the signal being indicative of the adhesive force between the item and the particle. To further specify the embodiment the particles are coated with a material. To further specify the embodiment groups of particles are coated with a groups of materials and other groups of particles are coated with other groups of materials. To further specify the embodiment the item is selected from the group consisting essentially of a cell, a live cell, a cell culture, extracellular matrix, a particle, a sphere, a cube, a block, a substrate, a surface, a device, a protein, an antibody. To further specify the embodiment the particles are selected from the group consisting essentially of a bead, a cell, a live cell, a circulating cell, microbead, antibody functionalized bead, a protein coated particle, a microparticle, a nano-particle, a particle, a sphere, a cube, a block, a device, a microsphere. To further specify the embodiment the material is selected from the group consisting essentially of antibodies, biological binders, proteins, ligands, peptides, bacteria, coatings, bio-molecules, molecules, organic molecules, inorganic molecules, polymers, or the like. To further specify the embodiment groups of particles with different coatings each group identifiable by color or florescent coding are distributed on item. To further specify the embodiment positive pressure is applied to remove the tip from the particle and the process is repeated in order to measure the adhesion between the item and another particle.

In one embodiment, a method to use a polymeric micro-arm apparatus is disclosed. The method comprising of an apparatus comprising of an elongated hollow polymeric structure with a distal end and a proximal end (such as a cantilever, a tube, or the like); an opening near the distal end (such as a tip of cone shaped with an opening); a main body attached to the polymeric structure (such as chip, a PCB, a silicon chip, an Su-8 chip, a glass substrate, a substrate); means to move the polymeric apparatus and the substrate in relation to each other (means include piezoelectric stage, motorized stage, manual stage, micro-manipulators and the like); means to monitor the movement of the polymeric apparatus and the surface in relation to each other (means include optical microscopes, video cameras, scanning electron microscopes, microscopes, CCD cameras, or the like); means to generate fluid flow through the opening and means to measure a flowrate of the fluid flow through the opening (such means are a pump, a flow meter, and a flow control valve to provide pressure, to control and measure the flow of a fluid through the hollow structure at the opening, these are connected with flexible tubes or directly connected to the apparatus; means to generate fluidic flow have a bi-directional capabilities able to create a pressure, a vacuum, positive and negative pressures); and an element embedded in the structure configured to output a signal indicative of the bending of the polymeric structure and a measure of the bending of the structure (such means have been described in this disclosure and include piezoelectric elements, piezoresistive elements, thin metal film elements like gold, gold/chrome, and the like, elastoresistive elements). To further specify the embodiment the apparatus is made of the polymeric structure material of construction selected from the group consisting essentially of a polymer, an elastomer, SU-8, polyimide, silicone, PDMS, and parylene. To further specify the embodiment the element is a resistor with a material of construction selected from the group consisting essentially of conductive polymer and metal thin film. To further specify the embodiment the element is a resistor configured to output an electrical signal indicative of a change of an electrical resistance, the change of the electrical resistance being a measure of polymeric structure bending. To further specify the embodiment the apparatus further comprises an electrode functionally attached inside the polymeric structure and another electrode in contact or in proximity with the surface (such electrodes have been described above). To further specify the embodiment the apparatus further comprises a resistor functionally attached inside the polymeric structure (such as a platinum resistor). To further specify the embodiment the resistor is configured to provide heating or to measure temperature. To further specify the embodiment the apparatus further comprises means to measure the movement of the polymeric apparatus and the surface in relation to each other.

To further specify the embodiment the method includes an item placed in proximity to a surface or on the surface; monitoring the signal of the element to determine contact between the apparatus and the item; and contacting the item with the apparatus at the opening, wherein the item is selected from the group consisting essentially of a cell, a sample, and a surface is claimed. To further specify the method includes delivering a fluid on the item is claimed. To further specify the method includes reacting the fluid to produce a solid material. To further specify the method includes heating the surface. To further specify the method includes functionally attaching an electrode inside the polymeric structure and contacting or bringing in close proximity another electrode to the surface. To further specify the method includes configuring the apparatus to selectably measure an ionic current or a membrane potential of ion channels on the item (similar to patch clamping).

To further specify the method includes placing a first item and a second item on a surface or in proximity to the surface near the apparatus, monitoring the signal to determine contact between the apparatus and the first item; contacting the first item at the opening; applying a pressure which is sufficient to functionally connect the first item to the opening; monitoring the signal to determine contact between the first item and the second item; contacting the second item with the first item. To specify the method includes a resistor configured to provide heating or to measure temperature. To further specify the method includes the first item and the second item are selected from the group consisting essentially of a cell, a live cell, a bead, a functionalized microbead, antibody functionalized bead, a circulating tumor cell, a suspended cell, a micro-particle, a nano-particle, an item, a particle, a sphere, a cube, a block, a substrate, a surface, or the like. To specify the method claimed includes after the contacting the second item to the first item step, adhering the first item to the second item, moving the polymeric structure and the surface away from each other, and measuring the strength of adhesion by monitoring and recording the signal of the element. To specify the method includes indentation and elastography measured by the element signal, in other words the element signal is indicative of the indentation if the structure is moved toward the particle and of adhesive force if the structure is moved away from the particle.

To further specify the method includes after the applying step, drawing the first item into the structure. To further specify the method includes after the contacting the second item to the first item step, applying positive pressure to the first item and depositing it onto the second item. To further specify the method claimed further the first item is configured to be identified with a distinct color or fluorescence.

To further specify the method includes placing an item on a surface; placing one or more particles on the item; bringing the polymeric structure and one of the particles close to each other, which then becomes a selected particle; monitoring the signal of the element to determine the contact between the apparatus and the particle; contacting the selected particle with the polymeric structure; applying pressure to attach the selected particle at the opening; pulling the selected particle away from the item; and measuring the output signal of the element, the signal being indicative of the adhesive force between the item and the particle. To further specify the method includes the particles are coated with a material. To further specify the method includes the particles are subdivided into groups and each group is coated with one or more distinct materials. To further specify the method includes the item being selected from the group consisting essentially of a cell, a live cell, a cell culture, extracellular matrix, a sphere, a cube, a block, a substrate, a surface, a surface, a device, a protein, and an antibody. To specify the method includes the particles being selected from the group consisting essentially of a bead, a cell, a live cell, a circulating cell, microbead, antibody functionalized bead, a protein coated particle, a micro-particle, a nano-particle, a sphere, a cube, a block, a device, and a microsphere. To specify the method includes the material is selected from the group consisting essentially of antibodies, biological binders, proteins, ligands, peptides, bacteria, coatings, bio-molecules, molecules, organic molecules, inorganic molecules, and polymers. To specify the method includes the particle group coatings are identifiable by color or fluorescent coding. To specify the method comprises after the last step, applying a positive pressure to discharge the particle from the opening. To specify the method includes the polymeric structure material of construction is selected from the group consisting essentially of a polymer, an elastomer, SU-8, polyimide, silicone, PDMS, and parylene. To specify the method claimed further the element is a resistor with a material of construction selected from the group consisting essentially of conductive polymer and metal thin film. To specify the method claimed further the element is a resistor configured to output an electrical signal indicative of a change of an electrical resistance, the change of the electrical resistance being a measure of polymeric structure bending. To specify the method claimed further the apparatus further comprises an electrode functionally attached inside the polymeric structure and another electrode in contact or in proximity with the surface. To specify the method claimed further the apparatus further comprises a resistor functionally attached inside the polymeric structure. To specify the method claimed further the resistor is configured to provide heating or to measure temperature. To specify the method claimed further the apparatus further comprises means to measure the movement of the polymeric apparatus and the surface in relation to each other.

In multiple embodiments the micro-arm is also called an elongated hollow polymeric structure, a hollow cantilever, pipette, micro-pipette, micro-aspiration needle, a fluidic cantilever, a cantilever with a fluidic channel, an elongated hollow polymeric structure, a hollow beam anchored at only one end. The cantilever can be of any shape, for example cylindrical, cube, rectangular, rectangular prism, or the like. In multiple embodiments the substrate of the hollow polymeric structure is also referred to as the main body. In multiple embodiments a surface is also referred to as a substrate, glass slide, sample holder, Petri dish, dish, glass slide, micro-well plate, micro well, ELISA well plate, plate, or the like. In multiple embodiments a pumping unit is used as means to generate fluidic flow with bi-directional capabilities able to create a pressure, a vaccum, positive and negative pressures.

The features and advantages of the present invention described in the embodiments are presented for illustrative purposes only and should not be construed to limit the scope of the invention. Many modifications and variations of these embodiments are possible. To illustrate, one can shrink the dimensions of the pipette or certain features to submicron or smaller to nanometer features. One or two or all three dimensions may be in the submicron range.

While the invention has been thus described with reference to the embodiments, it will be readily understood by those skilled in the art that equivalents may be substituted for the various elements and modifications made without departing from the spirit and scope of the invention. It is to be understood that all technical and scientific terms used in the present invention have the same meaning as commonly understood by one of ordinary skill in the art to which this invention belongs.

All patents and publications mentioned in the prior art are indicative of the levels of those skilled in the art to which the invention pertains. All patents and publications are herein incorporated by reference to the same extent as if each individual publication was specifically and individually indicated to be incorporated by reference, to the extent that they do not conflict with this disclosure.

While the present invention has been described with reference to exemplary embodiments, it will be readily apparent to those skilled in the art that the invention is not limited to the disclosed or illustrated embodiments but, on the contrary, is intended to cover numerous other modifications, substitutions, variations, and broad equivalent arrangements.

The invention claimed is:

1. A polymeric micro-arm apparatus, the apparatus comprising:
    an elongated hollow polymeric structure with a distal end and a proximal end;
    an opening near the distal end;
    a main body attached to the elongated hollow polymeric structure;
    means to move the polymeric micro-arm apparatus in relation to a surface;
    means to monitor the relative movement of the polymeric micro-arm apparatus and the surface;
    means to generate fluid flow through the opening;
    means to measure a flowrate of the fluid flow through the opening; and
    an element embedded in the elongated hollow polymeric structure and configured to output a signal, wherein the signal indicates an amount of polymeric structural bending.

2. The apparatus of claim 1, wherein the polymeric structure material of construction is selected from the group consisting of a polymer, an elastomer, SU-8, polyimide, silicone, PDMS, and parylene.

3. The apparatus of claim 1, wherein the element is a resistor with a material of construction selected from the group consisting of conductive polymer and metal thin film.

4. The apparatus of claim 1, wherein the element is a resistor configured to output an electrical signal indicative of a change of an electrical resistance, the change of the electrical resistance being a measure of polymeric structure bending.

5. The apparatus of claim 1, wherein the apparatus further comprises an electrode functionally attached inside the polymeric structure and another electrode in contact or in proximity with the surface.

6. The apparatus of claim 1, wherein the apparatus further comprises a resistor functionally attached inside the polymeric structure.

7. The apparatus of claim 6, wherein the resistor is configured to provide heating or to measure temperature.

8. The apparatus of claim 1, wherein the apparatus further comprises means to measure the movement of the polymeric apparatus and the surface in relation to each other.

* * * * *